(12) United States Patent
Harats et al.

(10) Patent No.: US 8,916,378 B2
(45) Date of Patent: *Dec. 23, 2014

(54) POLYNUCLEOTIDE CONSTRUCTS, PHARMACEUTICAL COMPOSITIONS AND METHODS FOR TARGETED DOWNREGULATIONS OF ANGIOGENESIS AND ANTICANCER THERAPY

(71) Applicant: Vascular Biogenics Ltd., Or Yehuda (IL)

(72) Inventors: Dror Harats, Ramat Gan (IL); Shoshana Greenberger, Petach Tikva (IL); Eyal Breitbart, Hashmonaim (IL)

(73) Assignee: Vascular Biogenics Ltd., Or Yehuda (IL)

( * ) Notice: Subject to any disclaimer, the term of this patent is extended or adjusted under 35 U.S.C. 154(b) by 0 days.

This patent is subject to a terminal disclaimer.

(21) Appl. No.: 13/785,863

(22) Filed: Mar. 5, 2013

(65) Prior Publication Data

US 2013/0272998 A1    Oct. 17, 2013

Related U.S. Application Data

(62) Division of application No. 13/163,767, filed on Jun. 20, 2011, now Pat. No. 8,415,318, which is a division of application No. 12/222,439, filed on Aug. 8, 2008, now Pat. No. 7,989,427, which is a division of application No. 10/490,746, filed as application No. PCT/IL02/00339 on May 1, 2002, now Pat. No. 7,585,666.

(60) Provisional application No. 60/330,118, filed on Oct. 19, 2001.

(51) Int. Cl.
| | |
|---|---|
| *C12N 15/00* | (2006.01) |
| *A61K 48/00* | (2006.01) |
| *C12N 5/00* | (2006.01) |
| *C12N 5/02* | (2006.01) |
| *A61K 38/17* | (2006.01) |
| *A61K 31/711* | (2006.01) |
| *A61K 38/19* | (2006.01) |
| *C12N 15/86* | (2006.01) |

(52) U.S. Cl.
CPC ........... *A61K 38/191* (2013.01); *A61K 48/0008* (2013.01); *A61K 48/00* (2013.01); *C12N 2840/20* (2013.01); *C12N 2800/108* (2013.01); *A61K 38/1793* (2013.01); *A61K 31/711* (2013.01); *C12N 2830/008* (2013.01); *C12N 2830/15* (2013.01); *C12N 15/86* (2013.01); *A61K 38/177* (2013.01); *C12N 2830/85* (2013.01); *C12N 2710/10343* (2013.01)
USPC .............. 435/320.1; 514/44 R; 435/325

(58) Field of Classification Search
CPC ............ A61K 38/177; A61K 48/0008; A61K 38/191; A61K 38/1793; A61K 31/711; A61K 48/00; C12N 15/86; C12N 2710/10343; C12N 2800/108; C12N 2830/15; C12N 2830/85; C12N 2840/20; C12N 2830/008
USPC ..................... 435/85.1, 320.1, 325; 514/44 R
See application file for complete search history.

(56) References Cited

U.S. PATENT DOCUMENTS

| | | | |
|---|---|---|---|
| 4,866,042 | A | 9/1989 | Neuwelt |
| 5,686,281 | A | 11/1997 | Roberts |
| 5,734,039 | A | 3/1998 | Calabretta et al. |
| 5,747,340 | A | 5/1998 | Harats et al. |
| 5,792,453 | A | 8/1998 | Hammond et al. |
| 5,830,880 | A | 11/1998 | Sedlacek et al. |
| 5,882,893 | A | 3/1999 | Goodearl |
| 5,916,763 | A | 6/1999 | Williams et al. |
| 6,066,624 | A | 5/2000 | Woo et al. |
| 6,200,751 | B1 | 3/2001 | Gu et al. |
| 6,204,055 | B1 | 3/2001 | Dean et al. |
| 6,239,151 | B1 | 5/2001 | Broadhurst et al. |
| 6,265,216 | B1 | 7/2001 | Bennett et al. |

(Continued)

FOREIGN PATENT DOCUMENTS

| | | |
|---|---|---|
| JP | 2002/516568 | 6/2002 |
| JP | 2003-501367 A | 1/2003 |

(Continued)

OTHER PUBLICATIONS

Adachi, Y., et al., "A Midkine Promoter-Based Conditionally Replicative Adenovirus for Treatment of Pediatric Solid Tumors and Bone Marrow Tumor Purging," *Cancer Research* 61(21):7882-7888, American Association for Cancer Research, United States (2001).

(Continued)

*Primary Examiner* — Thaian N Ton
(74) *Attorney, Agent, or Firm* — Sterne Kessler Goldstein & Fox P.L.L.C.

(57) ABSTRACT

A novel nucleic acid construct for down-regulating angiogenesis in a tissue of a subject is provided. The nucleic acid construct includes: (a) a first polynucleotide region encoding a chimeric polypeptide including a ligand binding domain fused to an effector domain of an apoptosis signaling molecule; and (b) a second polynucleotide region encoding a cis acting regulatory element being for directing expression of the chimeric polypeptide in a specific tissue or cell; wherein the ligand binding domain is selected such that it is capable of binding a ligand present in the specific tissue or cell, whereas binding of the ligand to the ligand binding domain activates the effector domain of the apoptosis signaling molecule. Also provided are methods of utilizing this nucleic acid construct for treating diseases characterized by excessive or aberrant neo-vascularization or cell growth.

20 Claims, 9 Drawing Sheets

(56) References Cited

U.S. PATENT DOCUMENTS

| | | | |
|---|---|---|---|
| 6,300,490 B1 | 10/2001 | Huber et al. |
| 6,348,209 B2 | 2/2002 | Placke et al. |
| 6,503,886 B1 | 1/2003 | Baird et al. |
| 6,545,048 B1 | 4/2003 | Patterson et al. |
| 6,576,265 B1 | 6/2003 | Spievack |
| 6,579,697 B1 | 6/2003 | Wallach et al. |
| 6,627,189 B1 | 9/2003 | Roth et al. |
| 6,783,776 B2 | 8/2004 | Spievack |
| 7,579,327 B2 | 8/2009 | Harats et al. |
| 7,585,666 B2 | 9/2009 | Harats et al. |
| 7,625,558 B2 | 12/2009 | Greene et al. |
| 7,989,427 B2 | 8/2011 | Harats et al. |
| 8,039,261 B2 | 10/2011 | Harats et al. |
| 8,071,740 B2 | 12/2011 | Harats et al. |
| 8,206,743 B2 | 6/2012 | Harats et al. |
| 8,415,318 B2 | 4/2013 | Harats et al. |
| 2003/0124100 A1 | 7/2003 | Harats |
| 2003/0194802 A1 | 10/2003 | Itskovitz-Eldor et al. |
| 2003/0195338 A1 | 10/2003 | Chung et al. |
| 2004/0044403 A1 | 3/2004 | Bischoff et al. |
| 2004/0048280 A1 | 3/2004 | Harats |
| 2004/0170975 A1 | 9/2004 | Savitzky et al. |
| 2004/0197860 A1 | 10/2004 | Harats et al. |
| 2004/0224389 A1 | 11/2004 | Bellgrau et al. |
| 2005/0112110 A1 | 5/2005 | Harats |
| 2005/0186179 A1 | 8/2005 | Harats et al. |
| 2006/0057113 A1 | 3/2006 | Holm |
| 2006/0204478 A1 | 9/2006 | Harats et al. |
| 2007/0286845 A1 | 12/2007 | Harats et al. |
| 2008/0063656 A1 | 3/2008 | Emini et al. |
| 2009/0232808 A1 | 9/2009 | Priest et al. |
| 2009/0326052 A1 | 12/2009 | Harats et al. |
| 2010/0081193 A1 | 4/2010 | Breitbart et al. |
| 2010/0282634 A1 | 11/2010 | Harats et al. |
| 2010/0298226 A1 | 11/2010 | Breitbart et al. |
| 2011/0129511 A1 | 6/2011 | Harats et al. |
| 2011/0201677 A1 | 8/2011 | Harats et al. |
| 2011/0207985 A1 | 8/2011 | Harats et al. |
| 2011/0251122 A1 | 10/2011 | Harats et al. |
| 2011/0319479 A1 | 12/2011 | Breitbart et al. |
| 2012/0201790 A1 | 8/2012 | Harats et al. |
| 2013/0011367 A1 | 1/2013 | Harats et al. |
| 2013/0052165 A1 | 2/2013 | Bangio et al. |
| 2013/0209450 A1 | 8/2013 | Cohen et al. |
| 2013/0272998 A1 | 10/2013 | Harats et al. |
| 2013/0280216 A1 | 10/2013 | Cohen et al. |
| 2013/0280217 A1 | 10/2013 | Cohen et al. |
| 2013/0295053 A1 | 11/2013 | Bangio et al. |
| 2013/0296404 A1 | 11/2013 | Harats et al. |
| 2013/0303595 A1 | 11/2013 | Cohen et al. |

FOREIGN PATENT DOCUMENTS

| | | |
|---|---|---|
| WO | WO 95/05835 A1 | 3/1995 |
| WO | WO 98/39465 A2 | 9/1998 |
| WO | WO 00/06759 | 2/2000 |
| WO | WO 01/83560 A1 | 11/2001 |
| WO | WO 02/10368 A1 | 2/2002 |
| WO | WO 03/000928 A2 | 1/2003 |
| WO | WO 03/033514 A1 | 4/2003 |
| WO | WO 03/038043 A2 | 5/2003 |
| WO | WO 03/039458 A2 | 5/2003 |
| WO | WO 03/093409 A2 | 11/2003 |
| WO | WO 2004/031357 A2 | 4/2004 |
| WO | WO 2004/035616 A2 | 4/2004 |
| WO | WO 2004/061458 A2 | 7/2004 |
| WO | WO 2011/086509 A1 | 7/2011 |
| WO | WO 2012/052878 A1 | 4/2012 |

OTHER PUBLICATIONS

Adams, M. and Thomas, H., "A phase I study of the matrix metalloproteinase inhibitor, marimastat, administered concurrently with carboplatin, to patients with relapsed ovarian cancer," *Proceedings American Society of Clinical Oncology 17*:217a, American Society of Clinical Oncology, United States (1998).

Aird, W.C., et al., "Human von Willebrand factor gene sequences target expression to a subpopulation of endothelial cells in transgenic mice," *Proc. Natl. Acad. Sci. 92*(110):4567-4571, The National Academy of Sciences, United States (1995).

Alon, T., et al., "Vascular endothelial growth factor acts as a survival factor for newly formed retinal vessels and has implications for retinopathy of prematurity," *Nature Medicine 1*(10):1024-1028, Nature Publishing Group, England (1995).

Alpern-Elran, H., et al., "Angiogenic activity of the atherosclerotic carotid artery plaque," *J. Neurosung. 70*:942-945, American Association of Neurological Surgeons, United States (1989).

Anderson, W. F., "Human Gene Therapy," *Nature 392*:25-30, Nature Publishing Group, England (1998).

Aoki, M., et al., "In Vivo Transfer Efficiency of Antisense Oligonucleotides into the Myocardium Using HVJ-Liposome Method," *Biochem. Biophys. Res. Commun. 231*(3):540-545, Academic Press, United States (1997).

Araki, T. and Milbrandt, J., "Ninjurin2, A Novel Homophilic Adhesion Molecule, Is Expressed in Mature Sensory and Enteric Neurons and Promotes Neurite Outgrowth," *J. Neurosci. 20*(1):187-195, Society for Neuroscience, United States (2000).

Arap, W., et al., "Cancer Treatment by Targeted Drug Delivery to Tumor Vasculature in a Mouse Model," *Science 279*(5349):377-380, American Association for the Advancement of Science, United States (1998).

Ausprunk, D.H., and Folkman, J., "Migration and Proliferation of Endothelial Cells in Performed and Newly Formed Blood Vessels during Tumor Angiogenesis," *Microvascular Research 14*(1):53-65, Academic Press, Inc., United States (1977).

Bangari, D.S. and Mittal, S.K., "Current Strategies and Future Directions for Eluding Adenoviral Vector Immunity," *Current Gene Therapy 6*(2):215-226, Bentham Science, United States (2006).

Barcelos, L.S., et al., "Impaired Inflammatory Angiogenesis, but Not Leukocyte Influx, in Mice Lacking TNFR1," *Journal of Leukocyte Biology 78*:352-358, Society for Leukocyte Biology, United States (2005).

Becker, T. C., et al., "Use of Recombinant Adenovirus for Metabolic Engineering of Mammalian Cells," *Methods in Cell Biology 43*:161-189, Academic Press, Inc., United States (1994).

Benjamin, L.E. and Keshet, E., "Conditional switching of vascular endothelial growth factor (VEGF) expression in tumors: Induction of endothelial cell shedding and regression of hemangioblastoma-like vessels by VEGF withdrawal," *Proc. Natl. Acad. Sci. USA 94*:8761-8766, The National Academy of Sciences, United States (1997).

Benjamin, L.E., et al., "Selective ablation of immature blood vessels in established human tumors follows vascular endothelial growth factor withdrawal," *J. Clin. Invest. 103*(2):159-165, American Society for Clinical Investigation, United States (1999).

Bobek, V., et al., "Gene Therapy of the Ischemic Lower Limb—Therapeutic Angiogenesis," *Vascular Pharmacology 44*(6):395-405, Elsevier Inc., United States (2006).

Boldin, M.P., et al., "A Novel Protein That Interacts With the Death Domain of Fas/APO1 Contains a Sequence Motif Related to the Death Domain," *The Journal of Biological Chemistry 270*(14):7795-7798, The American Society and Molecular Biology, Inc., United States (1995).

Brenner, et al., "Antivascular Activity of VBIII in Glioblastoma Xenografts," *Journal of Clinical Oncology*, ASCO Annual Meeting Proceedings (Post Meeting Edition), 28(15 Suppl.): Abstract No. e13652, American Society of Clinical Oncology, United States (2010).

Bu, X. and Quertermous, T., "Identification of an Endothelial Cell-specific Regulatory Region in the Murine Enothelin-1 Gene," *The Journal of Biological Chemistry 272*(51):32613-32622, The American Society for Biochemistry and Molecular Biology, Inc., United States (1997).

Calabresi, P. and Chabner, B.A., "Antineoplastic Agents" *The Pharmacological Basis of Therapeutics 52*:1209-1263, 8th Edition, Pergamon Press, Inc., United States (1990).

(56) References Cited

OTHER PUBLICATIONS

Cameliet, P. and Conway, E. M., "Growing Better Blood Vessels," *Nature Biotechnology* 19:1019-1020, Nature Publishing Group, England (2001).

Celletti, F.L., et al., "Effect of Human Recombinant Vasular Endothelial Growth Factor$_{165}$ on Progression of Atherosclerotic Plaque," *Journal of the American College of Cardiology* 37(8):2126-2130, American College of Cardiology, Elsevier Science, Inc., United States (2001).

Chen, Y.-H., et al., "Upstream Stimulatory Factors Regulate Aortic Preferentially Expressed Gene-1 Expression in Vascular Smooth Muscle Cells," *The Journal of Biological Chemistry* 276(50):47658-47663, The American Society for Biochemistry and Molecular Biology, Inc., United States (2001).

Chi, A. S., et al., "Angiogenesis as a Therapeutic Target in Malignant Gliomas," *The Oncologist* 14(6):621-636, AlphaMed Press, AlphaMed Press, United States (2009).

Cho, J., et al., "Development of an Efficient Endothelial Cell Specific Vector Using Promoter and 5' Untranslated Sequences From the Human Proproendothelin-1 Gene," *Experimental and Molecular Medicine* 35(4):269-274, Korean Biochemistry and Medical biochemistry and Molecular Biology, Korea (2003).

Collins, C. J., et al., "Molecular Cloning of the Human Gene for Von Willebrand Factor and Identification of the Transcription Initiation Site," *Proc. Natl. Acad. Sci.* 84:4393-4397, The National Academy of Sciences, United States (1987).

Collins, T., el al., "Strucutre and Chromosomal Location of the Gene for Endothelial- Leukocyte Adhesion Molecule I," *The Journal of Biological Chemistry* 266(4):2466-2473, The American Society for Biochemistry and Molecular Biology, Inc., United States (1991).

Couffinhal, T. et al., "Animal Model: Mouse Model of Angiogenesis," *American Journal of Pathology* 152(6):1667-1679, American Society for Investigative Pathology, United States (1998).

Dancer, A., et al., "Expression of Thymidine Kinase Driven by an Endothelial-Specific Promoter Inhibits Tumor Growth of Lewis Lung Carcinoma Cells in Transgenic Mice," *Gene Therapy* 10(14):1170-1178, Nature Publishing Group, England (2003).

Davis, C.G., "The Many Faces of Epidermal Growth Factor Repeats," *The New Biologist* 2(5):410-419, W.B. Saunders, United States (1990).

Denekamp, J. and Hobson, B., "Endothelial-Cell Proliferation in Experimental Tumours," *Br. J. Cancer* 46:711-720, Nature Publishing Group, England (1982).

Deonarain, M.P., "Ligand-Targeted Receptor-Mediated Vectors for Gene Delivery," *Expert Opinion on Therapeutic Patents* 8(1):53-69,Informa Healthcare, Ashley Publications Ltd., England (1998).

De Palma, M., et al., "Targeting exogenous genes to tumor angiogenesis by transplantation of genetically modified hematopoietic stem cells," *Nature Medicine* 9(6):789-795, Nature Publishing Group, England (2003).

Dor, Y., et al., "Induction of Vasular Networks in Adult Organs: Implications to Proangiogenic Therapy," *Annals of the NY Academy of Sciences* 995:208-216, New York Academy of Sciences, United States (2003).

Dulak, J., et al., "Vascular Endothelial Growth Factor: Angiogenesis, Atherogenesis or Both?," *Journal of the American College of Cardiology* 38(7):2137-2138, Elsevier Biomedical, United States (2001).

Epstein, S. E., et al., "Therapeutic interventions for enhancing collateral development by administration of growth factors: basic principles, early results and potential hazards," *Cardiovascular Research* 49:532-542, Elsevier Science B.V., Netherlands (2001).

Fang, B. and Roth, J.A., "The role of gene therapy in combined modality treatment strategies for cancer," *Current Opinion in Molecular Therapeutics* 5(5):475-482, Current Drugs, England (2003).

Faries, P. L., et al., "Assessing the Role of Gene Therapy in the Treatment of Vascular Disease," *Annals of Vascular Surgery* 14(2):181-188, Elsevier B.V., Netherlands (2000).

Feldman, A.L., et al., "Progress in Antiangiogenic Gene Therapy of Cancer," *Cancer* 89(6):1181-1194, American Cancer Society, United States (2000).

Fiers, W., et al., "The Human Fibroblast and Human Immune Interferon Genes and Their Expression in Homologous and Heterologous Cells," *Phil. Trans. R. Soc. Lond. B.* 299(1094):29-38, The Royal Society, England (1982).

Folkman, J., "Angiogenesis and apoptosis," *Seminars in Cancer Biology* 13(2):159-167, Elsevier Science Ltd., England (2003).

Folkman, J., "How is Blood Vessel Growth Regulated in Norman and Neoplastic Tissue?—G.H.A. Clowes Memorial Award Lecture," *Cancer Research* 46(2):467-473, American Association for Cancer Research, United States (1986).

Folkman, J., "Role of angiogenesis in tumor growth and metastasis," *Semin Oncol* 29(6):15-18, Elsevier Science, United States (2002).

Folkman, J., "Seminars in Medicine of the Beth Israel Hospital, Boston: Clinical Applications of Research on Angiogenesis," *The New England Journal of Medicine* 333(26):1757-1763, Massachusetts Medical Society, United States (1995).

Folkman, J., "Toward an understanding of angiogenesis: search and discovery," *Perspectives in Biology and Medicine* 29:10-36, The University of Chicago Press, United States (1985).

Frey-Tag, et al., "Gene Therapy Strategies to Enhance the Effectiveness of Cancer Radiotherapy," *Current Opinion in Molecular Therapeutics* 6(5):513-524, The Thomson Corporation, United States (2004).

Funatsu, H., et al., "Increased Levels of Vascular Endothelial Growth Factor and Interleukin-6 in the Aqueous Humor of Diabetics with Macular Edema," *Am. J. Opthalmol.* 133(1):70-77, Elsevier Science Inc., United States (2002).

Garlanda, C. and Dejana, E., "Heterogeneity of Endothelial Cells," *Arteriosclerosis, Thrombosis, and Vascular Biology* 17(7):1193-1202, American Heart Association, Inc., United States (1997).

Gilboa, E., et al., "Transfer and expression of cloned genes using retroviral vectors," *BioTechniques* 4(6):504-512, Eaton Publishing Co., United States (1986).

Goltsev, Y. V., et al., "CASH, A Novel Caspase Homologue With Death Effector Domains," *The Journal of Biological Chemistry* 272(32):19641-19644, The American Society for Biochemistry and Molecular Biology, United States (1997).

Gôrecki, D. C., "'Dressed-Up' Naked Plasmids: Emerging Vectors for Non-Viral Gene Therapy," *Discovery Medicine* 6(35):191-197, Solariz, United States (2008).

Gorski, D.H., et al., "Potentiation of the Antitumor Effect of Ionizing Radiation by Brief Concomitant Exposures to Angiostatin," *Cancer Research* 58(24):5686-5689, American Association for Cancer Research, United States (1998).

Gowdak, L.H.W., et al., "Adenovirus-Mediated VEGF$_{121}$ Gene Transfer Stimulates Angiogenesis in Normoperfused Skeletal Muscle and Preserves Tissue Perfusion After Induction of Ischemia," *Circulation* 102:565-571, American Heart Association, United States (2000).

Gray, P. W., et al., "Cloning of Human Tumor Necrosis Factor (TNF) Receptor cDNA and Expression of Recombinant Soluble TNF-Binding Protein," *Proc. Natl. Acad. Sci.* 87:7380-7384, The National Academy of Sciences, United States (1990).

Greenberger, S., et al., "Transcription-Controlled Gene Therapy Against Tumor Angiogenesis," *The Journal of Clinical Investigation* 113(7):1017-1024, American Society for Clinical Investigation., United States (2004).

Gridley, D. S., et al., "Combining Gene Therapy and Radiation Against Cancer," *Current Gene Therapy* 4(3):281-284, Bentham Science Publishers, Netherlands (2004) (Abstract Only).

Gu, J., et al., "HTERT promoter induces tumor-specific Bax gene expression and cell killing in syngenic mouse tumor model and prevents systemic toxicity," *Gene Therapy* 9(1):30-37, Nature Publishing Group, England (2002).

Hahn, A.W.A., et al., "Effects of Peptide Vasoconstrictors on Vessel Structure," *The American Journal of Medicine* 94(4A):13S-19S, Association of Professors of Medicine, United States (1993).

(56) References Cited

OTHER PUBLICATIONS

Hammond, H.R. and McKirnan, M.D., "Angiogenic gene therapy for heart disease: a review of animal studies and clinical trials," *Cardiovascular Research* 49:561-567, Elsevier Science B.V., Netherlands (2001).

Hanahan, D., "Signaling Vascular Morphogenesis and Maintenance," *Science* 277:48-50, American Association for the Advancement of Science, United States (1997).

Harada, K., et al., "Basic Fibroblast Growth Factor Improves Myocardial Function in Chronically Ischemic Porcine Hearts," *J. Clin. Invest.* 94:623-630, The American Society for Clinical Investigation, Inc., United States (1994).

Harats, D., et al., "Targeting Gene Expression to the Vascular Wall in Transgenic Mice Using the Murine Preproendothelin-1 Promoter," *J. Clin. Invest.* 95(3):1335-1344, The American Society for Clinical Investigation, Inc., United States (1995).

Harrigan, M.R., et al., "Intraventricular Infusion of Vascular Endothelial Growth Factor Promotes Cerebral Angiogenesis with Minimal Brain Edema," *Neurosurgery* 50(3):589-598, Lippincott Williams & Wilkins, United States (2002).

Herbst, R.S., et al., "Angiogenesis Inhibitors in Clinical for Lung Cancer," *Seminars in Oncology* 29(1):66-77, Elsevier Science, United States (2002).

Hoefer, I. E., et al., "Direct Evidence for Tumor Necrosis Factor-α Signaling Arteriogenesis," *Circulation* 105(14):1639-1641, American Heart Association, Inc., United States (2002).

Horley, K. J., et al., "Molecular cloning of murine intercellular adhesion molecule (ICAM-1)," *EMBO. J.* 8(10):2889-2896, IRL Press, United States (1989).

Hsu, S., et al., "Platelet-Derived Growth Factor-B Increases Colon Cancer Cell Growth In Vivo by a Paracrine Effect," *Journal of Cellular Physiology* 165:239-245, Wiley-Liss, Inc., United States (1995).

Hu, J., et al., "Hypoxia Regulates Expression of the Endothelial-1 Gene Through a Proximal-Inducible Factor-1 Binding Site on the Antisence Strand," *Biophysical and Biophysical Research Communication* 245(3):894-899, Academic Press, United States (1998).

Iademarco, M. F., et al., "Characterization of the promoter for vascular cell adhesion molecule-1 (VCAM-1)," *The Journal of Biological Chemistry* 267(23):16323-16329, The American Society for Biochemistry and Molecular Biology, Inc. (1992).

Iris, F. J., et al., "Dense Alu Clustering and a Potential New Member of the NFB Family Within a 90 Kilobase HLA Class III Segment," *Nature Genetics* 3:137-145, Nature Publishing Group, England (1993).

Itasaka, S., et al., "Endostatin Blocks Endothelial Repopulation After Radiation Therapy," *Proceedings of the American Association for Cancer Research* 44(2):22, American Association for Cancer Research, United States (2003).

Jäger, U., et al., "Endothelial Cell-Specific Transcriptional Targeting from a Hybrid Long Terminal Repeat Retrovirus Vector Containing Human Prepro-Endothelin-1 Promoter Sequences," *Journal of Virology* 73(12):9702-9709, American Society for Microbiology, United States (1999).

Jaggar, R.T., et al, "Endothelial Cell-Specific Expression of Tumor Necrosis Factor-α from the KDR or E-Selectin Promoters Following Retroviral Delivery," *Human Gene Therapy* 8:2239-2247, Mary Ann Liebert, Inc., United States (1997).

Jones, D., et al., "A Portable Regulatory Element Directs Specific Expression of the *Caenorhabditis elegans* Ubiquitin Gene UBQ-2 in the Somatic Gonad," *Developmental Biology* 171:60-72, Academic Press, Inc., United States (1995).

Jornot, L., et al, "*N*-Acetylsyteine Augments Adenovirus-Mediated Gene Expression in Human Endothelial Cells by Enhancing Transgene Transcription and Virus Entry," *The Journal of Gene Medicine* 4(1):54-65, John Wiley & Sons, Ltd., England (2002).

Joshi, P., et al., "Endothelial Cells Adhere to the RGD Domain and the Fibrinogen-Like Terminal Knob of Tenascin," *Journal of Cell Science* 106:389-400, The Company of Biologists Limited, Great Britain (1993).

Juengst, E. T., "What Next for Human Gene Therapy? Gene Transfer often has multiple and unpredictable effects on cells," *BMJ* 326:1410-1411, BMJ Publishing Group, Ltd., England (2003).

Kaiser; M., et al., "Platelet-Derived Growth Factor, Intimal Hyperplasia, and Ischemic Complications in Giant Cell Arteritis," *Arthritis & Rheumatism* 41(4):623-633, American College of Rheumatology, United States (1998).

Kaito, T., et al., "Potentiation of the activity of bone morphogenetic protein-2 in bone regeneration by a PLA-PEG/hydroxyapatite composite," *Biomaterials* 26(1):73-79, Elsevier Ltd., England (2005).

Kambara, H., et al., "Combined radiation and gene therapy for brain tumors with adenovirus-mediated transfer of *cytosine deaminase* and *uracil phosphoribosyltransferase* genes," *Cancer Gene Therapy* 9:840-845, Nature Publishing Group, England (2002).

Kaplan, H. J., et al., "Fas Ligand (CD95 Ligand) Controls Angiogenesis Beneath the Retina," *Nature Medicine* 5(3):292-297, Nature Publishing Group, England (1999).

Katabi, M. M., et al., "Hexokinase Type II: A Novel Tumor-Specific Promoter for Gene-Targeted Therapy Differentially Expressed and Regulated in Human Cancer Cells," *Human Gene Therapy* 10:155-164, Mary Ann Liebert, Inc., United States (1999).

Kay, M. A., et al., "Viral Vectors for Gene Therapy: The Art of Turning Infectious Agents Into Vehicles of Therapeutics," *Nature Medicine* 7(1):33-40, Nature Publishing Group, England (2001).

Kaye, F. J., et al., "A single amino acid substitution results in a retinoblastoma protein defective in phosphorylation and oncoprotein binding," *Proc. Natl. Acad. Sci.* 87:6922-6926, The National Academy of Sciences, United States (1990).

Khan, T. A., et al., "Gene therapy progress and prospects: therapeutic angiogenesis for limb and myocardial ischemia," *Gene Therapy* 10:285-291, Nature Publishing Group, England (2003).

Kim, P. K. M., et al., "Hepatocyte Fas-associating Death Domain Protein/Mediator of Receptor-induced Toxicity (FADD/MORT1) Levels Increase in Response to Pro-apoptotic Stimuli," *The Journal of Biological Chemistry* 277(41):38855-38862, The American Society for Biochemistry and Molecular Biology, Inc., United States (2002).

Kim, W. J., et al., "Effect of PDGF, IL-1α, and BMP2/4 on Corneal Fibroblast Chemotaxis: Expression of the Platelet-Derived Growth Factor System in the Cornea," *Investigative Ophthalmology & Vision Science* 40(7):1364-1372, Association for Research in Vision and Ophthalmology, Association for Research in Vision and Ophthalmology, United States (1999).

Kodama, K., et al, "The Features and Shortcomings for Gene Delivery of Current Non-Viral Carriers," *Current Medicinal Chemistry* 13(18):2155-2161, Bentham Science Publishers, Netherlands (2006).

Kolesnick, R. and Fuks, Z., "Radiation and Ceramide-Induced Apoptosis," *Oncogene* 22:5897-5906, Nature Publishing Group, England (2003).

Kong, H.-L. and Crystal, R. G., "Gene Therapy Strategies for Tumor Antiangiogenesis," *Journal of the National Cancer Institute* 90(4):273-286, Oxford University Press, England (1998).

Korhonen, J., et al., "Endothelial-Specific Gene Expression Directed by the *tie*Gene Promoter In Vivo," *Blood* 86(5):1828-1835, The American Society of Hematology, United States (1995).

Koshikawa, N., et al., "Therapeutic Efficacy of the Suicide Gene Driven by the Promoter of Vascular Endothelial Growth Factor Gene Against Hypoxic Tumor Cells," *Cancer Research* 60(11):2936-2941, American Association for Cancer Research, United States (2000).

Koyama, N., et al., "Migratory and Proliferative Effect of Platelet-Dervied Growth Factor in Rabbit Retinal Endothelial Cells: Evidence of an Autocrine Pathway of Platelet-Derived Growth Factor," *Journal of Cellular Physiology* 158:1-6, Wiley-Liss, Inc., United States (1994).

Kronenwett, R., et al., "Oligodeoxyribonucleotide Uptake in Primary Human Hematopoietic Cells is Enhanced by Cationic Lipids and Depends on the Hematopoietic Cell Subset," *Blood* 91(3):852-862, The American Society of Hematology, United States (1998).

Kwong, Y.-L., et al., "Combination Therapy With Suicide and Cytokine Genes for Hepatic Metastases of Lung Cancer," *CHEST* 112(5):1332-1337, The American College of Chest Physicians, United States (1997).

(56) References Cited

OTHER PUBLICATIONS

Lahav, R., et al., "Endothelin Receptor B Inhibition Triggers Apoptosis and Enhances Angiogenesis in Melanomas," *Cancer Research* 64:8945-8953, American Association for Cancer Research, United States (2004).

Lavigne, C. and Thierry, A. R., "Enhanced Antisense Inhibition of Human Immunodeficiency Virus Type I in Cell Cultures by DLS Delivery System," *Biochemical and Biophysical Research Communications* 237(3):566-571, Academic Press, United States (1997).

Layne, M. D., et al., "Characterization of the Mouse Aortic Carboxypeptides-Like Protein Promoter Reveals Activity in Differentiated and Dedifferentiated Vascular Smooth Muscle Cells," *Circulation Research* 90:728-736, American Heart Association, Inc., United States (2002).

Lebedeva, I. .V., et al., "Restoring apoptosis as a strategy for cancer gene therapy: focus on *p53* and *mda-7*," *Seminars in Cancer Biology* 13(2):169-178, Elsevier Science Ltd., England (2003).

Lee, M.-E., et al., "Functional Analysis of the Endothelin-1 Gene Promoter," *Journal of Biological Chemistry* 265(18):10446-10450, The American Society for Biochemistry and Molecular Biology, Inc., United States (1990).

Li, X. R., et al., "Transcriptional Regulation of Fas Gene Expression by GA-Binding Protein and AP-I in T Cells Antigen Receport CD3 Complex-Stimulated T Cells," *The Journal of Biological Chemistry* 274(49):35203-35210, The American Society for Biochemistry and Molecular Biology, Inc., United States (1999).

Liu, M. W., et al., "Restenosis After Coronary Angioplasty. Potential Biologic Determinants and Role of Intimal Hyperplasia," *Circulation* 79:1374-1387, American Heart Association, Inc., United States (1989).

Lowe, C., et al., "Osteopetrosis in Src-Deficient Mice is Due to an Autonomous Defect of Osteoclasts," *Proc. Natl. Acad. Sci.* 90:4485-4489, The National Academy of Sciences, United States (1993).

Luft, F. C., "Making sense out of antisense oligodeoxynucleotide delivery: getting there is half the fun," *J. Mol. Med.* 76(2):75-76, Springer-Verlag, Germany (1998).

Lyden, D., et al., "Impaired Recruitment of Bone-Marrow-Derived Endothelial and Hematopoietic Precursor Cells Blocks Tumor Angiogenesis and Growth," *Nature Medicine* 7(11):1194-1201, Nature Publishing Group, England (2001).

Mariani, et al., "Anti-angiogenesis: the challenges ahead," *MedGenMed* 5(2):22, MedScape, United States (2003).

Micheau, O., et al., "STAT-1-Independent Upregulation of FADD and Procaspase-3 and -8 in Cancer Cells Treated with Cytotoxic Drugs," *Biochemical and Biophysical Research Communications* 256(3):603-607, Academic Press, United States (1999).

Minchenko, A. and Caro, J., et al., "Regulation of endothelin-1 gene expression in human microvascular endothelial cells by hypoxia and cobalt: Role of hypoxia responsive element," *Molecular and Cellular Biochemistry* 208(1-2):53-62, Kluwer Academic Publishers, Netherlands (2000).

Modlich, U., et al., "Increasing endothelial cell specific expression by the use of heterologous hypoxic and cytokine-inducible enhancers," *Gene Therapy* 7896-902, Macmillan Publishers Ltd., England (2000).

Morimoto, E., et al., "Adenovirus-mediated suicide gene transfer to small cell lung carcinoma using a tumor-specific promoter," *Anticancer Research* 21:329-331, International Institute of Anticancer Research, Greece (2001).

Morishia, K., et al., "A Novel Promoter for Vascular Endothelial Growth Factor Receptor (Flt-1) That Confers Endothelial-Specific Gene Expression," *The Journal of Biological Chemistry* 270(46):27948-27953, The American Society for Biochemistry and Molecular Biology, Inc., United States (1995).

Murata, T., et al., "Vascular Endothelium has a Local Anti-Andenovirus Vector System and Glucocorticoid Optimizes Its Gene Transduction," *Arterioscler Thromb. Vasc. Biol.* 25:1796-1803, American Heart Association, Inc., United States (2005).

Nayak, S., et al., "Progress and Prospects: Immune Responses to Viral Vectors," *Gene Therapy* 17(3):295-304, Advance Online Publication, Nature Publishing Group, England (2009).

NCBI Entrez, GenBank Report, Accession No. AR005095, Harats, D., et al., Entry Date Dec. 1998.

Nesbit, M., et al., "$\alpha 5$ and $\alpha 2$ Integrin Gene Transfers Mimic the PDGF-B—Induced Transformed Phenotype of Fibroblasts in Human Skin," *Laboratory Investigation* 81(9):1263-1274, The United States and Canadian Academy of Pathology, Inc., United States (2001).

Nettelbeck, D.M., et al., "Targeting of Adenovirus to Endothelial Cells by Bispecific Single-Chain Diabody Directed against the Adenovirus Fiber Knob Domain and Human Endoglin (CD105)," *Molecular Therapy* 3(6):882-891, The American Society of Gene Therapy, United States (2001).

Newman, P. J., et al., "PECAM-1 (CD31) cloning and relation to adhesion molecules of the immunoglobulin gene superfamily," *Science* 247(4947):1219-1222, American Association for the Advancement of Science, United States (1990).

Nicklin, S. A., et al., "Selective Targeting of Gene Transfer to Vascular Endothelial Cells by Use of Peptide Isolated by Phage Display," *Circulation* 102:231-237, American Heart Association, Inc., United States (2000).

Nicosia, R. and Ottinetti, A., "Growth of Microvessels in Serum-Free Matrix Culture of Rat Aorta: A Quantitative Assay of Angiogensis In vitro," *Laboratory Investigation* 63(1):115-122, The United State and Canadian Academy of Pathology, Inc., United States (1990).

Nicosia, R. F., et. al., "Modulation of Angiogenesis in Vitro by Laminin-Entactin Complex," *Developmental Biology* 164:197-206, Academic Press, Inc., United State (1994).

Nishikawa, T., et al., "Adenovirus-Mediated mda-7 (IL24) Gene Therapy Suppresses Angiogenesis and Sensitizes NSCLC Xenograft Tumors to Radiation," *Molecular Therapy* 9(6):818-828, The American Society of Gene Therapy, United States (2004).

O'Reilly, M. S., et al., "Endostatin: An Endogenous Inhibitor of Angiogenesis and Tumor Growth," *Cell* 88(2):277-285, Cell Press, United States (1997).

Ozaki, K., et al., "Use of von to Willebrand Factor Promoter to Transduce Suicidal Gene to Human Endothelial Cells, HUVEC," *Human Gene Therapy* 7:1483-1490, Mary Ann Liebert, Inc., United States (1996).

Ozawa. T., et al, "Histologic Changes of Nonbiodegradable and Biodegradable Biomaterials Used to Repair Right Ventricular Heart Defects in Rats," *The Journal of Thoracic and Cardiovascular Surgery* 124(6):1157-1164, The American Association for Thoracic Surgery, United States (2002).

Paku, S. and Paweletz, N., "First Steps of Tumor-Related Angiogenesis," *Laboratory Investigation* 65(3)334-346, The United States and Canadian Academy of Pathology, Inc., United States (1991).

Palù, G., at al., "In pursuit of new developments for genetherapy of human diseases," *Journal of Biotechnology* 68(1):1-13, Elsevier Science B.V., Netherlands (1999).

Papadakis, E. D., et al., "Promoters and Control Elements: Designing Expression Cassettes for Gene Therapy," *Current Gene Therapy* 4:89-113, Bentham Science Publishers Ltd., Netherlands (2004).

Patan, S., at al., "Intussusceptive Microvascular Growth in a Human Colon Adenocarcinoma Xenograft: A Novel Mechanism of Tumor Angiogenesis," *Microvascular Research* 51(2):260-272, Academic Press, United States (1996).

Patil, S. D., et al., "DNA-based Therapeutics and DNA Delivery Systems: A Comprehensive Review," *The AAPS Journal* 7(1):E61-E77, American Association of Pharmaceutical Scientists, United States (2005).

Peled, M., et al., "Antiangiogenic systemic gene therapy combined with doxorubicin administration induced caspase 8 and 9-mediated apoptosis in endothelial cells and an anti-metastasis effect," *Cancer Gene Therapy* 15:535-542, Nature Publishing Group, England (2008).

Peled, M., et al., "Systemic Administration of a Conditionally Replicating Adenovirus, Targeted to Angiogenesis, Reduced Lung

(56) References Cited

OTHER PUBLICATIONS

Metastasis Burden in Cotton Rats," *Clinical Cancer Research* 15(5):1664-1673, American Association for Cancer Research, United States (2009).

Peng, X.Y., et al., "The Use of the L-Plastin Promoter for Adenoviral-mediated, Tumor-specific Gene Expression in Ovarian and Bladder Cancer Cell Lines," *Cancer Research* 61(11):4405-4413, American Association for Cancer Research, United States (2001).

Penland, S. K., et al., "Combining Anti-VEGF Approaches With Oxaliplatin in Advanced Colorectal Cancer," *Clinical Colorectal Cancer Supplement* 4(2):S74-S80, Elsevier Inc., United States (2004).

Percy, M. J., et al, "Sequence Analysis of the 3' Hypoxia-Responsive Element of the Human Erythropoietin Gene in Patients with Erythrocytosis," *Biochemical and Molecular Medicine* 62:132-134, Academic Press, United States (1997).

Printz, M. A., et al, "Fibroblast Growth Factor 2-Retargeted Adenoviral Vectors Exhibit a Modified Biolocalization Pattern and Display Reduced Toxicity Relative to Native Adenoviral Vectors," *Human Gene Therapy* 11:191-204, Mary Ann Liebert, Inc., United States (2000).

Rein, D. T., et al., "Current developments in adenovirus based cancer gene therapy," *Future Oncol.* 2:137-143, Future Medicine Ltd., England (2006).

Risau, W., "Mechanisms of Angiogenesis," *Nature* 386:671-674, Nature Publishing Group, England (1997).

Ríus, C., et al., "Cloning of the Promoter Region of Human Endoglin, the Target Gene for Hereditary Hemorrhagic Telangiectasia Type I," *Blood* 92(12):4677-4690, The American Society of Hematology, United States (1998).

Roberts, D.M. et al., "Hexon-chimaeric adenovirus serotype 5 vectors circumvent pre-existing anti-vector immunity," *Nature* 441:239-243, Nature Publishing Group, England (2006).

Ronicke, V., et al., "Characterization of the endothelium-specific murine vascular endothelial growth factor receptor-2 (Flk-1) promoter," *Circulation Research* 79(2):277-285, American Heart Association, Inc., United States (1996).

Rosengart, T.K., et al., "Six-month assessment of a phase I trial of angiogenic gene therapy for the treatment of coronary artery disease using direct intramyocardial administration of an adenovirus vector expressing the VEGF121 cDNA," *Annals of Surgery* 230(4):466-472, Lippincott Williams & Wilkins, Inc., United States (1999).

Roskoski, Jr., R., "Sunitinib: A VEGF and PDGF receptor protein kinase and angiogenesis inhibitor," *Biochemical and Biophysical Research Communications* 356:323-328, Elsevier Inc., United States (2007).

Sano, H., et al., "Functional Blockade of Platelet-Derived Growth Factor Receptor-β But Not of Receptor-α Prevents Vascular Smooth Muscle Cell Accumulation in Fibrous Cap Lesions in Apolipoprotein E-Defictent Mice," *Circulation* 103:2955-2960, American Heart Association, Inc., United States (2001).

Sato, T. N., et al., "tie-i and tie-2 define another class of putative receptor tyrosine kinase genes expressed in early embryonic vascular system," *Proc. Natl. Acad. Sci.* 90:9355-9358, The National Academy of Sciences, United States (1993).

Savontaus, M. J., et al., "Transcriptional targeting of conditionally replicating adenovirus to dividing endothelial cells," *Gene Therapy* 9(14):972-979, Nature Publishing Group, England (2002).

Schlaeger, et al., "Vascular Endothelial Cell Lineage-Specific Promoter in Transgenic Mice," *Development* 121:1089-1098, The Company of Biologists Limited, Great Britain (1995).

Schlaeger, T.M., et al., "Uniform vascular-endothelial-cell-specific gene expression in both embryonic and adult transgenic mice," *Proc. Natl. Acad. Sci. USA* 94:3058-3063, The National Academy of Sciences of the USA, United States (1997).

Schramek, H., et al., "Interactions of the vasoconstrictor peptides, angiotensin II and endothelin-I, with vasodilatory prostaglandins," *Seminars in Nephrology* 15(3):195-204, W.B. Saunders Company, United States (1995).

Semenza, G.L., et al., "Hypoxia, HIF-1, and the pathophysiology of the common human diseases," *Adv. Exp. Med. Biol.* 475:123-130, Kluwer Academic/Plenum Publishers, United States (2000).

Shimo, T., et al., "Connective tissue growth factor as a major angiogenic agent that is induced by hypoxia in a human breast cancer cell line," *Cancer Letters* 174:57-64, Elsevier Science Ireland Ltd., Ireland (2001).

Shir, A. and Levitzki, A., "Gene Therapy for Glioblastoma: Future Perspective for Delivery Systems and Molecular Targets," *Cellular and Molecular Neurobiology* 21(6):645-656, Plenum Publishing Corporation, United States (2001).

Simovic, D., et al., "Improvement in Chronic Ischemic Neuropathy After Intramuscular phVEGF$_{165}$ Gene Transfer in Patients with Critical Limb Ischemia," *Arch. Neurol.* 58:761-768, American Medical Association, United States (2001).

Smallwood, S., et al., "Different Substitutions at Conserved Amino Acids in Domains II and III in the Sendai L RNA Polymerase Protein Inactive Viral RNA Synthesis," *Virology* 304:135-145, Elsevier Science (USA), United States (2002).

Smythe, W. R., et al., "Treatment of Experimental Human Mesothelioma Using Adenovirus Transfer of the Herpes Simplex Thymidine Kinase Gene," *Annals of Surgery* 222(1):78-86, Lippincott-Raven Publishers, United States (1995).

Soriano, P., et al., "Targeted disruption of the c-src proto-oncogene leads to osteopetrosis in mice," *Cell* 64(4):693-702, Cell Press, United States (1991).

Staba, M. J., et al., "Adenoviral TNF-α gene therapy and radiation damage tumor vasculature in a human malignant glioma xenograft," *Gene Therapy* 5:293-300, Stockton Press, United States (1998).

Stefanidakis, M., et al., "Identification of a Negatively Charged Peptide Motif within the Catalytic Domain of Progelatinases That Mediates Binding to Leukocyte β$_2$ Integrins," *The Journal of Biological Chemistry* 278(36):34674-34684, The American Society for Biochemistry and Molecular Biology, Inc., United States (2003).

Strasser, A., et al., "Apoptosis Signaling," *Annual Review of Biochemistry* 69:217-245, Annual Reviews, United States (2000).

Sukhatme, V.P., et al., "A Novel Early Growth Response Gene Rapidly Induced by Fibroblast, Epithelial Cell and Lymphocyte Mitogens," *Oncogene Research* 1:343-355, Harwood Academic Publishers GmbH, Switzerland (1987).

Sun, G., et al., "Functional Analysis of the Preproendothelin-1 Gene Promoter in Pulmonary Epithelial Cells and Monocytes," *Biochemical and Biophysical Research Communications* 221(3):647-652, Academic Press, United States (1996).

Takayama, K., et al., "Vascular Endothelial Growth Factor Promoter-Based Conditionally Replicative Adenoviruses for Pan-Carcinoma Application," *Cancer Gene Therapy* 14(1):105-116, Nature Publishing Group, England (2007).

Theodosis, D. T., "Oxytocin-Secreting Neurons: A Physiological Model of Morphological Neuronal and Glial Plasticity in the Adult Hypothalamus," *Frontiers in Neuroendocrinology* 23:101-135, Elsevier Science, United States (2002).

Thickett, D.R., "Vascular Endothelial Growth Factor May Contribute to Increased Vascular Permeability in Acute Respiratory Distress Syndrome," *Am. J. Respir. Crit. Care Med.* 164:1601-1605, American Thoracic Society, United States (2001).

Thompson, J. A., et al., "Heparin-binding growth factor 1 induces the formation of organoid neovascular structures in vivo," *Proc. Natl. Acad. Sci. USA* 86:7928-7932, The National Academy of Sciences, United States (1989).

Tomasinsig, L. and Zanetti, M., "The Cathelicidins—Structure, Function and Evolution," *Current Protein and Peptide Science* 6:23-34, Bentham Science Publishers Ltd., Netherlands (2005).

Tkiozzi, P., and Giles, F., "A Phase I Study to Assess the Safety and Distribution of GT-111 in Patients With Advanced Metastatic Cancer," *Vascular Biogenics, Ltd.*, Clinical Trials (2009).

Unger, E.F., et al., "Basic fibroblast growth factor enhances myocardial collateral flow in a canine model," *American Journal of Physiology* 266(4):H1588-H1595, The American Physiological Society, United States (1994).

Van De Stolpe, A., and Van Der Saag, P.T., "Intercellular Adhesion Molecule-1," *Journal of Molecular Medicine* 74(1):13-33, Springer-Verlag, Germany (1996) (Abstract Only).

(56) References Cited

OTHER PUBLICATIONS

Varda-Bloom, N., et al., "Tissue-specific gene therapy directed to tumor angiogenesis," *Gene Therapy* 8(11);819-827, Nature Publishing Group, England (2001).
Verma, I. M. and Somia, N., "Gene Therapy—Promises, Problems and Prospects," *Nature* 389(6648):239-242, Nature Publishing Group, England (1997).
Wachsberger, P., et al., "Tumor Response to Ionizing Radiation Combines With Antiangiogenesis or Vascular Targeting Agents: Exploring Mechanisms of Interaction," *Clinical Cancer Research* 9:1957-1971, American Association for Cancer Research, United States (2003).
Wadhwa, P. D., et al., "Cancer Gene Therapy: Scientific Basic," *Annual Review of Medicine* 53:437-453, Annual Reviews, United States (2002).
Wang, et al., "Molecular Cloning of the Complementary DNA for Human Tumor Necrosis Factor," *Science* 228(4696):149-154, American Association for the Advancement of Science, United States (1985).
Watkins, S. J., et al., "The 'adenobody' approach to viral targeting: specific and enhanced adenoviral gene delivery," *Gene Therapy* 4(10):1004-1012, Stockton Press, United States (1997).
West, D. C. and Kumar, S., et al., "Endothelial Cell Proliferation and Diabetic Retinopathy," *The Lancet* 331(8587):715-716, Lancet Publishing Group, England (1988).
Whitaker, et al., "Induction of Functional Neovascularization by Wisker Stimulation After Focal Ischemia," *33rd Annual Meeting of the Society of Neuroscience*, Society of Neuroscience, United States (2003) (Abstract Only).
Williams, K. J., et al., "Hypoxia and oxidative stress in breast cancer Tumour hypoxia—therapeutic consideration," *Breast Cancer Research* 3:328-331, BioMed Center Ltd., Current Science, England (2001).
Wong, G. G., et al., "Human GM-CSF: Molecular Cloning of the Complementary DNA and Purification of the Natural and Recombinant Proteins," *Science* 228(4701):810-815, American Association for the Advancement of Science, United States (1985).
Wu, L., et al., "Chimeric PSA Enhancer Exhibit Augments Activity in Prostate Cancer Therapy Vectors," *Gene Therapy* 8(18):1416-1426, Nature Publishing Group, England (2001).
Yanagisawa, M., et al., "A novel potent vasoconstrictor peptide produced by vascular endothelial cells," *Nature* 332:411-415, Nature Publishing Group, England (1988).
Yangagisawa-Miwa, A., et al., "Salvage of Infarcted Myocardium by Angiogenic Action of Basic Fibroblast Growth Factor," *Science* 257(5075):1401-1403, American Association for the Advancement of Science, United States (1992).
Yang, M., et al., "Whole-body and intravital optical imaging of angiogenesis in orthotopically implanted tumors," *PNAS* 98(5):2616-2621, The National Academy of Sciences, United States (2001).
Young, D., "VBL Focuses on Inflammatory Market With Novel Phospholipids," *BioWorld Today* 21(3):1-7, AHC Media LLC, United States (2010).
Zhang, Z.-L., et al., "Current Strategies and Future Directions of Antiangiogenic Tumor Therapy" *Acta Biochimica et Biophysica Sinica* 35(10):873-880, China Academic Journal Electronic Publishing House, China (2003).
Zou, Y., et al., "Antitumor Activity of Free and Liposome-Entrapped Annamycin, a Lipophilic Anthracycline Antibiotic With Non-Cross-Resistance Properties," *Cancer Research* 54:1479-1484, American Association for Cancer Research, United States (1994).
European Search Report and the European Search Opinion for European Application No. 09168899.4, European Patent Office, The Hague, Netherlands, mailed on May 17, 2010.
European Search Report and the European Search Opinion for European Application No. 10185193.9, European Patent Office. The Hague, Netherlands, mailed on Oct. 18, 2011.
European Search Report and the European Search Opinion for European Application No. 10177257.2, European Patent Office, The Hague, Netherlands, mailed on Jan. 19, 2011.
European Search Report and the European Search Opinion for European Application No. 10185195.4, European Patent Office, The Hague, Netherlands, mailed on Feb. 22, 2011.
European Search Report and the European Search Opinion for European Application No. 10184033.8, European Patent Office, The Hague, Netherlands, mailed on Feb. 24, 2011.
European Search Report and the European Search Opinion for European Application No. 09176343.3, European Patent Office, The Hague, Netherlands, mailed on Jul. 29, 2010.
International Search Report for International Application No. PCT/IL02/00339, Patent Cooperation Treaty, mailed on Dec. 2, 2002.
International Search Report for International Application No. PCT/IL05/01195, Patent Cooperation Treaty, mailed on Aug. 4, 2006.
International Search Report for International Application No. PCT/IL07/00242, Patent Cooperation Treaty, mailed on Sep. 18, 2008.
International Search Report for International Application No. PCT/IL08/00543, Patent Cooperation Treaty, mailed on Apr. 29, 2009.
International Search Report for International Application No. PCT/IL01/01059, Patent Cooperation Treaty, mailed on May 4,2004.
International Search Report Search Report for International Application No. PCT/IL03/00347, Patent Cooperation Treaty, mailed on Jan. 28, 2005.
Search Report and Written Opinion Dated Oct. 7, 2010 From the Intellectual Property Office of Singapore Issued by the Austrian Patent Office Re. Application No. 200907209-1.
Search Report and Written Opinion Dated Apr. 21, 2009 From the Intellectual Property Office Singapore Issued by the Austrian Patent Office Re. Application No. 200703466-3.
Supplementary European Search Report and the European Search Opinion for European Application No. EP 05806361, European Patent Office, The Hague, Netherlands, mailed on Oct. 17, 2007.
Supplementary European Search Report for European Application No. EP 02 80 1473, European Patent Office, Munich, Germany, mailed on Mar. 8, 2006.
Supplementary European Search Report for European Application No. EP 03 71 7516, European Patent Office, Munich, Germany, mailed on Oct. 14, 2005.
Supplementary European Search Report for European Application No. EP 02801473.6, European Patent Office, The Hague, Netherlands, mailed on Mar. 21, 2006.
Supplementary European Search Report for European Application No. EP 03717516, European Patent Office, The Hague, Netherlands, mailed on Oct. 28, 2005.
Supplementary Partial European Search Report Dated Nov. 15, 2004 from the European Patent Office Re.: Application EP 01996590.4.
Partial European Search Report for European Application No. 09168899.4 , European Patent Office, The Hague, Netherlands, mailed on Feb. 23, 2010.
International Search Report and the Written Opinion for International Application No. PCT/IL2011/00009, Patent Cooperation Treaty, mailed on May 20, 2011.
International Search Report and the Written Opinion International Application No. PCT/IL2011/00007, Patent Cooperation Treaty, mailed on Sep. 1, 2011.
Communication Relating to the Results of the Extended International Search Dated Apr. 8, 2010 From the European Patent Office Re.: Application No. 09174998.6.
International Preliminary Examination Report for International Application No. PCT/IL01/01059, Patent Cooperation Treaty, issued on Jan. 28, 2005.
International Preliminary Examination Report for International Application No. PCT/IL02/00339, Patent Cooperation Treaty, issued on Jan. 5, 2005.
International Preliminary Examination Report for International Application No. PCT/IL03/00347, Patent Cooperation Treaty, issued on May 26, 2005.
International Preliminary Report on Patentability for International Application No. PCT/IL2005/001195, Patent Cooperation Treaty, issued on May 24, 2007.
International Preliminary Report on Patentability for International Application No. PCT/IL2007/000242, Patent Cooperation Treaty, issued on Jan. 22, 2009.

(56) References Cited

OTHER PUBLICATIONS

International Preliminary Report on Patentability for International Application No. PCT/IL2008/000543, Patent Cooperation Treaty, issued on Nov. 12, 2009.
Notice of Allowance mailed Apr. 8, 2009, in U.S. Appl. No. 10/975,619, Dror Harats et al., filed Oct. 29, 2004.
Notice of Allowance mailed Feb. 10, 2012, in U.S. Appl. No. 13/018,447, Dror Harats et al., filed Feb. 1, 2011.
Notice of Allowance mailed Jan. 12, 2011, in U.S. Appl. No. 10/988,487, Dror Harats et al., filed Nov. 14, 2004.
Notice of Allowance mailed Jun. 11, 2009, in U.S. Appl. No. 10/490,746, Dror Harats et al., filed Apr. 12, 2004.
Notice of Allowance mailed Jun. 28, 2011, in U.S. Appl. No. 11/359,513, Dror Harats et al., filed Feb. 23, 2006.
Notice of Allowance mailed Mar. 21, 2012, in U.S. Appl. No. 13/094,900, Dror Harats et al., filed Apr. 27, 2011.
Notice of Allowance mailed on Jun. 2, 2011, in U.S. Appl. No. 10/988,487, Dror Harats et al., filed Nov. 14, 2004.
Notice of Grant mailed Aug. 31, 2010, in Mexican Patent Application No. PA/a/2004/003514.
Notice of Non-Compliant Amendment mailed Jul. 12, 2011, in U.S. Appl. No. 12/224,178, Dror Harats et al., filed Feb. 22, 2007.
Notice of Non-Complaint Amendment mailed Sep. 19, 2011, in U.S. Appl. No. 12/224,178, Dror Harats et al., filed Feb. 22, 2007.
Office Action mailed Jun. 14, 2012, in U.S. Appl. No. 13/163,767,Dror Harats et al., filed Jun. 20, 2011.
Office Action mailed on Apr. 6, 2007, in U.S. Appl. No. 10/975,619, Dror Harats et al., filed Oct. 29, 2004.
Office Action mailed on Apr. 9, 2008, in U.S. Appl. No. 10/490,746, Dror Harats et al., filed Apr. 12, 2004.
Office Action mailed on Apr. 10, 2008, in U.S. Appl. No. 10/975,619, Dror Harats et al., filed Oct. 29, 2004.
Office Action mailed on Apr. 13, 2012 in U.S. Appl. No. 13/098,512, Dror Harats et al., filed May 2, 2011.
Office Action mailed on Aug. 4, 2009, in U.S. Appl. No. 11/359,513, Dror Harats et al., filed Feb. 23, 2006.
Office Action mailed on Aug. 5, 2010, in U.S. Appl. No. 11/359,513, Dror Harats et al., filed Feb. 23, 2006.
Office Action mailed on Aug. 31, 2009, in U.S. Appl. No. 11/790,992, Dror Harats et al., filed Apr. 30, 2007.
Office Action mailed on Dec. 6, 2010, in U.S. Appl. No. 12/224,178, Dror Harats et al., filed Feb. 22, 2007.
Office Action mailed on Dec. 13, 2011, in U.S. Appl. No. 12/224,178, Dror Harats et al., filed Feb. 22, 2007.
Office Action mailed on Dec. 15, 2009, in U.S. Appl. No. 11/790,992, Dror Harats et al., flied Apr. 30, 2007.
Office Action mailed on Dec. 15, 2011, in U.S. Appl. No. 12/591,252, Eyal Breitbart et al., filed Nov. 13, 2009.
Office Action mailed on Dec. 23, 2009, in U.S. Appl. No. 12/222,439, Dror Harats et al., filed Aug. 8, 2008.
Office Action mailed on Dec. 29, 2006, in U.S. Appl. No. 10/490,746, Dror Harats et al., filed Apr. 12, 2004.
Office Action mailed on Jan. 4, 2008, in U.S. Appl. No. 10/988,487, Dror Harats et al., filed Nov. 14, 2004.
Office Action mailed on Jan. 14, 2010, in U.S. Appl. No. 11/359,513, Dror Harats et al., filed Feb. 23, 2006.
Office Action mailed on Jan. 22, 2010, in U.S. Appl. No. 12/457,200, Dror Harats et al., filed Jun. 3, 2009.
Office Action mailed on Jan. 26, 2011, in U.S. Appl. No. 11/359,513, Dror Harats et al., filed Feb. 23, 2006.
Office Action mailed on Jul. 6, 2010, in U.S. Appl. No. 11/790,992, Dror Harats et al., filed Apr. 30, 2007.
Office Action mailed on Jul. 8, 2010, in U.S. Appl. No. 10/988,487, Dror Harats et al., filed Nov. 14, 2004.
Office Action mailed on Jul. 10, 2007, in U.S. Appl. No. 10/490,746, Dror Harats et al., filed Apr. 12, 2004.
Office Action mailed on Jul. 12, 2011, in U.S. Appl. No. 12/591,252, Eyal Breitbart et al., filed Nov. 13, 2009.
Office Action mailed on Jul. 12, 2011, in U.S. Appl. No. 13/018,447, Dror Harats et al., filed Feb. 1, 2011.
Office Action mailed on Jul. 14, 2010, in U.S. Appl. No. 10/135,447, Dror Harats et al., filed May 1, 2002.
Office Action mailed on Jul. 29, 2009, in U.S. Appl. No. 10/490,746, Dror Harats et al., filed Apr. 12, 2004.
Office Action mailed on Jun. 4, 2010, in U.S. Appl. No. 12/457,200, Dror Harats et al., filed Jun. 3, 2009.
Office Action mailed on Jun. 24, 2009, in U.S. Appl. No. 12/222,439, Dror Harats et al., filed Aug. 8, 2008.
Office Action mailed on May 6, 2009, in U.S. Appl. No. 11/359,513, Dror Harats et al., filed Feb. 23, 2006.
Office Action mailed on May 13, 2010, in U.S. Appl. No. 12/222,439, Dror Harats et al., filed Aug. 8, 2008.
Office Action mailed on Nov. 10, 2010, in U.S. Appl. No. 12/457,200, Dror Harats et al., filed Jun. 3, 2009.
Office Action mailed on Nov. 12, 2009, in U.S. Appl. No. 10/988,487, Dror Harats et al., filed Nov. 14, 2004.
Official Action mailed on Nov. 14, 2008, in U.S. Appl. No. 10/490,746, Dror Harats et al., filed Apr. 12, 2004.
Office Action mailed on Nov. 17, 2011, in U.S. Appl. No. 13/098,512, Dror Harats et al., filed May 2, 2011.
Office Action mailed on Oct. 2, 2008, in U.S. Appl. No. 11/359,513, Dror Harats et al., filed Feb. 23, 2006.
Office Action mailed on Oct. 7, 2010, in U.S. Appl. No. 12/224,178, Dror Harats et al., filed Feb. 22, 2007.
Office Action mailed on Oct. 11, 2006, in U.S. Appl. No. 10/490,746, Dror Harats et al., filed Apr. 12, 2004.
Office Action mailed on Oct. 13, 2010, in U.S. Appl. No. 12/222,439, Dror Harats et al., filed Aug. 8, 2008.
Office Action mailed on Sep. 9, 2011, in U.S. Appl. No. 13/098,512, Dror Harats et al., filed May 2, 2011.
Office Action mailed on Sep. 26, 2011 in U.S. Appl. No. 13/018,447, Dror Harats et al., filed Feb. 1, 2011.
Response Dated Aug. 1, 2011 to Notice of Non-Compliant Amendment of Jul. 12, 2011 in U.S. Appl. No. 12/224,178.
Response Dated Apr. 12, 2010 to Official Action of Nov. 12, 2009 in U.S. Appl. No. 10/988,487.
Response Dated Apr. 14, 2010 to Official Action of Dec. 15, 2009 in U.S. Appl. No. 11/790,992.
Response Dated Apr. 14, 2011 to Official Action of Jan. 26, 2011 in U.S. Appl. No. 11/359,513.
Response Dated Apr. 22, 2010 to Official Action of Dec. 23, 2009 in U.S. Appl. No. 12/222,439.
Response Dated Aug. 8, 2011 to Official Action of Jul. 12, 2011 in U.S. Appl. No. 13/018,447.
Response Dated Aug. 12, 2010 to Official Action of May 13, 2010 in U.S. Appl. No. 12/222,439.
Response Dated Aug. 25, 2010 to Official Action of Jun. 4, 2010 in U.S. Appl. No. 12/457,200.
Response Dated Dec. 5, 2010 to Official Action of Aug. 5, 2010 in U.S. Appl. No. 11/359,513.
Response Dated Feb. 3, 2011 to Official Action of Nov. 10, 2010, in U.S. Appl. No. 12/457,200.
Response Dated Feb. 22, 2010 to Official Action of Jan. 22, 2010 in U.S. Appl. No. 12/457,200.
Response Dated Jan. 3, 2011 to Official Action of Oct. 13, 2010 in U.S. Appl. No. 12/222,439.
Response Dated May 5, 2011 to Official Action of Dec. 6, 2010 in U.S. Appl. No. 12/224,178.
Response Dated May 13, 2010 to Official Action of Jan. 14, 2010 in U.S. Appl. No. 11/359,513.
Response Dated Nov. 4, 2009 to Official Action of Aug. 4, 2009 in U.S. Appl. No. 11/359,513.
Response Dated Nov. 8, 2010 to Office Action of Oct. 7, 2010 in U.S. Appl. No. 12/224,178.
Response Dated Nov. 24, 2011 to Office Action of Sep. 26, 2011 in U.S. Appl. No. 13/018,447.
Response Dated Oct. 5, 2010 to Official Action of Jul. 6, 2010 in U.S. Appl. No. 11/790,992.
Response Dated Oct. 5, 2011 to Official Action of Jul. 12, 2010 in U.S. Appl. No. 12/591,252.
Response Dated Oct. 7, 2010 to Official Action of Jul. 8, 2010 in U.S. Appl. No. 10/988,487.

(56) References Cited

OTHER PUBLICATIONS

Response Dated Oct. 10, 2011 to Official Action of Sep. 9, 2011 in U.S. Appl. No. 13/098,512.
Response Date Oct. 18, 2011 to Notice of Non-Compliant Amendment of Sep. 19, 2011 in U.S. Appl. No. 12/224,178.
Restriction Requirement mailed on Apr. 6, 2012, in U.S. Appl. No. 13/163,767, Dror Harats et al., filed Jun. 20, 2011.
Summons to Attend Oral Proceedings Pursuant to Rule 115(1) EPC Dated Jul. 13, 2009 From the European Patent Office Re.: Application No. 05806361.1.
Summons to Attend Oral Proceedings Pursuant to Rule 115(1) EPC Dated Sep. 14, 2009 From the European Patent Office Re.: Application No. 02801473.6.
Written Opinion of the International Search Authority for International Application No. PCT /IL02/00339, Israel Patent Office, issue on Oct. 29, 2003.
Written Opinion of the International Search Authority for International Application No. PCT/IL01/01059, Israel Patent Office, issue on Nov. 2, 2004.
Written Opinion of the International Search Authority for International Application No. PCT/IL05/01195, Israel Patent Office, issue on Aug. 4, 2006.
Written Opinion of the International Search Authority for International Application No. PCT/IL07/00242, Israel Patent Office, issue on Sep. 18, 2008.
Written Opinion of the International Search Authority for International Application No. PCT/IL08/00543, Israel Patent Office, issue on Apr. 29, 2009.
Office Action mailed Dec. 7, 2011, in U.S. Appl. No. 13/094,900, Dror Harats et al., filed Apr. 27, 2011.
Office Action mailed Nov. 23, 2012, in U.S. Appl. No. 13/454,171, Dror Harats et al., filed Apr. 24, 2012.
Office Action mailed Jan. 4, 2008, in U.S. Appl. No. 10/988,487, Dror Harats et al., filed Nov. 14, 2004.
Office Action mailed Nov. 12, 2009, in U.S. Appl. No. 10/988,487, Dror Harats et al., filed Nov. 14, 2004.
Office Action mailed Jul. 8, 2010, in U.S. Appl. No. 10/988,487, Dror Harats et al., filed Nov. 14, 2004.
Office Action mailed Jan. 2, 2013, in U.S. Appl. No. 12/224,178, Dror Harats et al., filed Feb. 22, 2007.
English language Abstract of Japanese Patent Publication No. JP 2003-501367 A, European Patent Office, espacenet database—Worldwide (2003).
Lopez, C.A., et al., "Chemoinducible gene therapy: A strategy to enhance doxorubicin antitumor activity," *Molecular Cancer Therapeutics* 3(9):1167-1175, American Association for Cancer Research, United States (2004).
Li, Y. et al., "A Heptocellular Carcinoma-specific Adenovirus Variant, CV890, Eliminates Distant Human Liver Tumors in Combination with Doxorubicin," *Cancer Research* 61:6428-6436, American Association for Cancer Research, United States (2001).
Sebastian, M., et al., "Adenovirus-mediated interferon-β gene thereapy combined with radiotherapy synergistically inhibits lung tumor growth in mice," *Journal of Clinical Oncology* 22:7340, American Society of Clinical Oncology, United States (2004).
Score Search Results Details for U.S. Appl. No. 12/224,178, received in the Office Action dated Jan. 2, 2013, for U.S. Appl. No. 12/224,178, filed Aug. 20, 2008, pp. 26-27 of 617 and pp. 90-91 of 609.

Zhu. Z.B. et al., "Targeting lung cancer using an infectivity enhanced CXCR4-CRAd," *Lung Cancer* 55:145-156, Elsevier Ireland Ltd., Ireland (2007).
Tanaka, T. et al., "Viral Vector-targeted Antiangiogenic Gene Therapy Utilizing an Angiostatin Complementary DNA," *Cancer Research* 58:3362-3369, American Association for Cancer Research, United States (1998).
Office Action mailed Jun. 13, 2013, in U.S. Appl. No. 12/457,200, Dror Harats et al., filed Jun. 3, 2009.
Office Action mailed Jun. 17, 2013, in U.S. Appl. No. 13/094,900, Dror Harats et al., filed Apr. 27, 2011.
Office Action mailed Sep. 9, 2013, in U.S. Appl. No. 13/454,171, Dror Harats et al., filed Apr. 24, 2012.
Office Action mailed on Aug. 8, 2013, in U.S. Appl. No. 12/591,252, Eyal Breitbart et al., filed Nov. 13, 2009.
Office Action mailed on May 16, 2013, in U.S. Appl. No. 13/549,355, Dror Harats et al., filed Jul. 13, 2012.
Office Action mailed on Jun. 20, 2013, in U.S. Appl. No. 11/790,992, Dror Harats et al., filed Apr. 30, 2007.
Restriction Requirement mailed on Sep. 18, 2013, in U.S. Appl. No. 13/800,478, Dror Harats et al., filed Mar. 13, 2013.
Office Action mailed on Oct. 22, 2013, in U.S. Appl. No. 13/549,355, Dror Harats et al., filed Jul. 13, 2012.
Supplementary European Search Report and European Search Opinion for European Application No. 07713267.8, European Patent Office, Munich,Germany, mailed on Aug. 23, 2013.
Górecki, D.C., "Prospects and problems of gene therapy: an update," *Expert Opinion on Emerging Drugs*, 6(2):187-198, Informa Plc, United Kingdom (2001).
Tomasoni, S., et al., "Gene Therapy: How to Target the Kidney, Promises and Pitfalls," *Current Gene Therapy* 4:115-122, Bentham Science Publishers Ltd., United Arab Emirates (2004).
Thomas, C.E., et al., "Progress and Problems With the Use of Viral Vectors for Gene Therapy", *Nature Reviews: Genetics*, 4: 346-358, Nature Publishing Group, England (2003).
Eck, S.L. et al., "Gene-Based Therapy", *Goodman & Gilman's The Pharmacological Basis of Therapeutics*, 9th Ed., Section I(Ch.5): 77-101, McGraw-Hill, United States (1996).
Co-pending, U.S. Appl. No. 13/520,457 inventors Harats, D., et al., filed Jul. 3, 2012 (Not Published).
Co-pending, U.S. Appl. No. 14/059,426 inventors Harats, D., et al., filed Oct. 21, 2013 (Not Published).
Office Action mailed Dec. 17, 2012, in U.S. Appl. No. 13/549,355, Dror Harats et al., filed Jul. 13, 2012.
Office Action mailed Nov. 18, 2013, in U.S. Appl. No. 12/457,200, Dror Harats et al., filed Jun. 3, 2009.
Office Action mailed Dec. 27, 2013, in U.S. Appl. No. 13/800,478, Dror Harats et al., filed Mar. 13, 2013.
Office Action mailed Jan. 3, 2014, in U.S. Appl. No. 12/591,252, Dror Harats et al., filed Nov. 13, 2009.
Notice of Allowance mailed on Mar. 31, 2014, in U.S. Appl. No. 12/457,200, Dror Harats et al., filed Jun. 3, 2009.
Notice of Allowance mailed on Apr. 4, 2014, in U.S. Appl. No. 13/549,355, Dror Harats et al., filed Jul. 13, 2012.
Notice of Allowance mailed on Apr. 24, 2014, in U.S. Appl. No. 13/454,171, Dror Harats et al., filed Apr. 24, 2012.
Itoh N. et al., The polypeptide encoded by the cDNA for human cell surface antigen Fas can mediate apoptosis. *Cell*. 66(2):233-43 (1991), Elsevier, Inc., United States.
Office Action Action mailed on Jun. 6, 2014, in U.S. Appl. No. 12/591,252, Eyal Breitbart et al., filed Nov. 13, 2009.

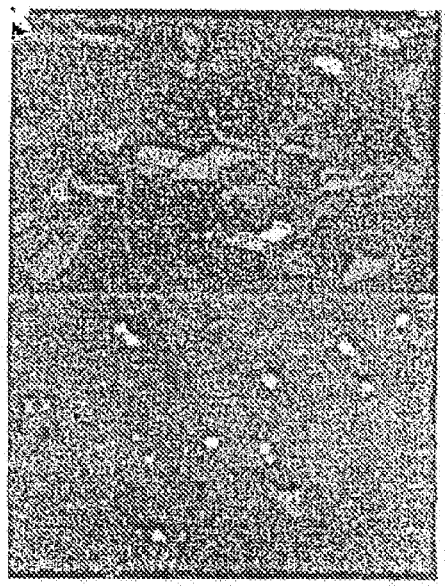
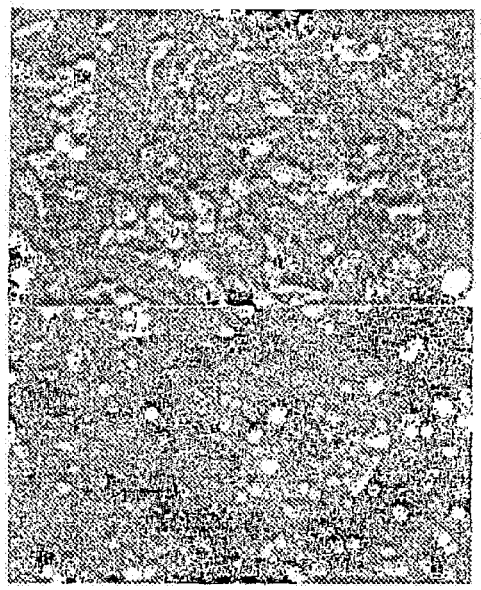
Fig. 2a                Fig. 2b
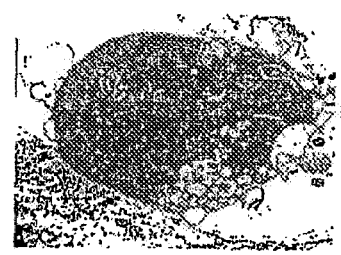
Fig. 3a
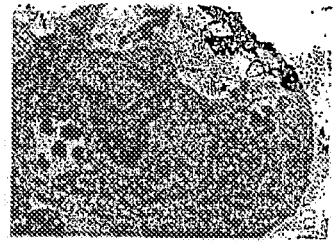
Fig. 3b
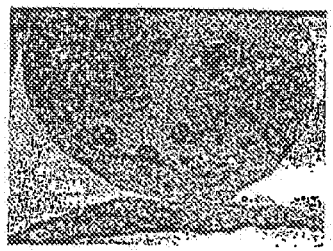
Fig. 3c
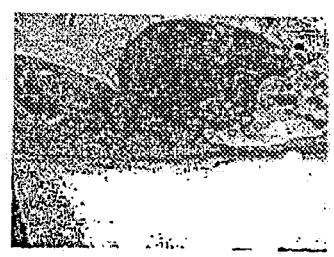
Fig. 3d
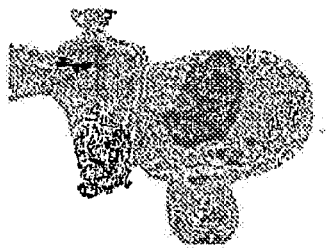
Fig. 3e
Fig. 3f Ad-PPE-Fas-c Ad-PPE-Luc

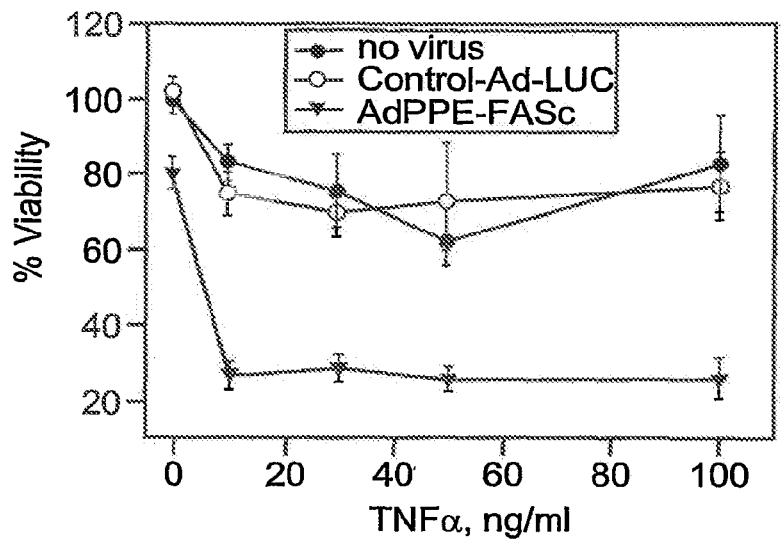
Fig. 8
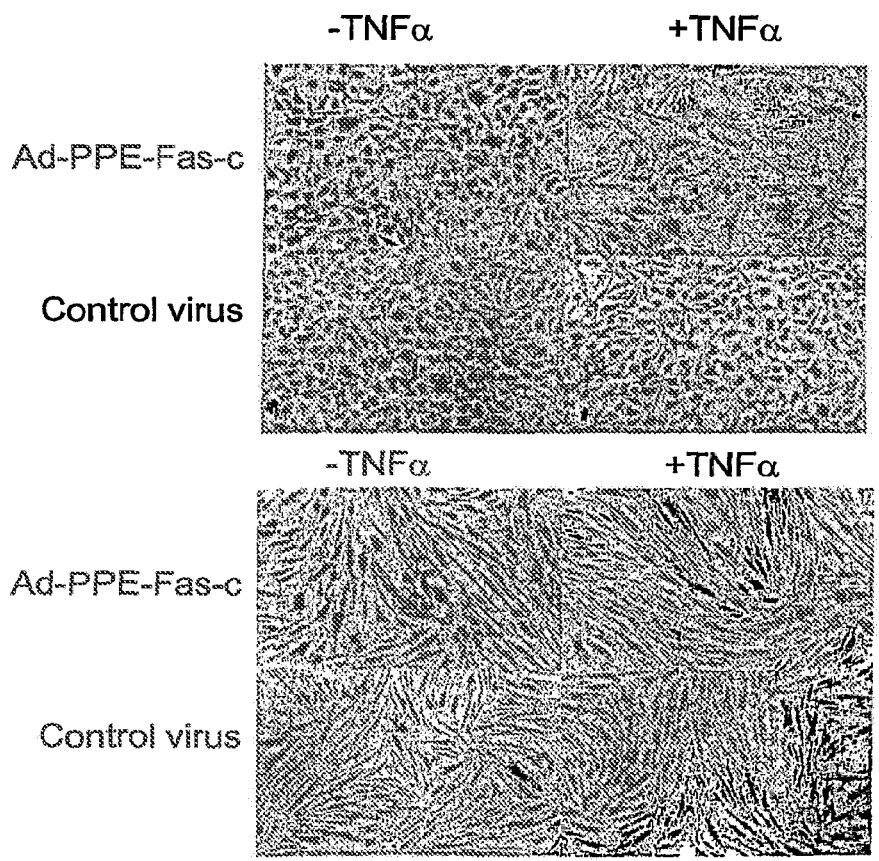
Fig. 9a
Fig. 9b

POLYNUCLEOTIDE CONSTRUCTS, PHARMACEUTICAL COMPOSITIONS AND METHODS FOR TARGETED DOWNREGULATIONS OF ANGIOGENESIS AND ANTICANCER THERAPY

RELATED APPLICATION/S

This application is a Divisional of U.S. patent application Ser. No. 13/163,767, filed on Jun. 20, 2011, which is a Divisional of U.S. patent application Ser. No. 12/222,439 filed on Aug. 8, 2008, now U.S. Pat. No. 7,989,427, which is a Divisional of U.S. patent application Ser. No. 10/490,746 filed on Apr. 12, 2004, now U.S. Pat. No. 7,585,666, which is a National Phase of PCT Patent Application No. PCT/IL02/00339 having International filing date of May 1, 2002, which claims the benefit of priority of U.S. Provisional Patent Application No. 60/330,118 filed on Oct. 19, 2001. The contents of the above applications are all incorporated herein by reference.

REFERENCE TO SEQUENCE LISTING SUBMITTED ELECTRONICALLY

The content of the electronically submitted sequence listing in ASCII text file (Name: 3182_0360004_SequenceListing_ascii; Size: 3,365 bytes; and Date of Creation: Mar. 5, 2013), filed herewith, is incorporated herein by reference in its entirety.

FIELD AND BACKGROUND OF THE INVENTION

The present invention relates to a nucleic acid constructs, pharmaceutical compositions and methods which can be used to downregulate angiogenesis in specific tissue regions of a subject. More particularly, the present invention relates to nucleic acid constructs, which can be used to activate apoptosis in specific cell subsets, thus, enabling treatment of diseases characterized by excessive or aberrant neovascularization or cell growth.

Angiogenesis is the growth of new blood vessels, a process that depends mainly on locomotion, proliferation, and tube formation by capillary endothelial cells. During angiogenesis, endothelial cells emerge from their quiescent state and proliferate rapidly. Although the molecular mechanisms responsible for transition of a cell to angiogenic phenotype are not known, the sequence of events leading to the formation of new vessels has been well documented [Hanahan, D., Science 277, 48-50, (1997)]. The vascular growth entails either endothelial sprouting [Risau, W., Nature 386, 671-674, (1997)] or intussusceptions [Patan, S., et al; Microvasc. Res. 51, 260-272, (1996)]. In the first pathway, the following sequence of events may occur: (a) dissolution of the basement of the vessel, usually a post capillary venule, and the interstitial matrix; (b) migration of endothelial cells toward the stimulus; (c) proliferation of endothelial cells trailing behind the leading endothelial cell (s); (d) formation of lumen (canalization) in the endothelial array/sprout; (e) formation of branches and loops by confluencial anastomoses of sprouts to permit blood flow; (f) investment of the vessel with pericytes (i.e., periendothelial cells and smooth muscle cells); and (g) formation of basement membrane around the immature vessel. New vessels can also be formed via the second pathway: insertion of interstitial tissue columns into the lumen of pre-existing vessels. The subsequent growth of these columns and their stabilization result in partitioning of the vessel lumen and remodeling of the local vascular network.

A variety of angiogenic factors govern the angiogenic process. It is understood that during pathology, the fine balance between pro-angiogenic factors and anti-angiogenic factors is disrupted, thereby eliciting nonself-limiting endothelial and periendothelial cell-proliferation. Until recently, the angiogenesis that occurs in diseases of ocular neovascularization, arthritis, skin diseases, and tumors, had been difficult to suppress therapeutically.

Therefore, the fundamental goal of all anti-angiogenic therapy is to return foci of proliferating microvessels to their normal resting state, and to prevent their regrowth [Cancer: Principles & Practice of Oncology, Fifth Edition, edited by Vincent T. DeVita, Jr., Samuel Hellman, Steven A. Rosenberg. Lippincott-Raven Publishers, Philadelphia. (1997)].

Anti-angiogenic therapy is a robust clinical approach, as it can delay the progression of tumor growth (e.g., retinopathies, benign and malignant angiogenic tumors).

In general, every disease caused by uncontrolled growth of capillary blood vessels such as diabetic retinopathy, psoriasis, arthritis, hemangiomas, tumor growth and metastasis is a target for anti-angiogenic therapy.

For example, the progressive growth of solid tumors beyond clinically occult sizes (e.g., a few $mm^3$) requires the continuous formation of new blood vessels, a process known as tumor angiogenesis. Tumor growth and metastasis are angiogenesis-dependent. A tumor must continuously stimulate the growth of new capillary blood vessels to deliver nutrients and oxygen for the tumor itself to grow. Therefore, either prevention of tumor angiogenesis or selective destruction of tumor's existing blood vessels (vascular targeting therapy) underlies anti-angiogenic tumor therapy.

Recently, a plethora of anti-angiogenic agents has been developed for the treatment of malignant diseases, some of which are already under clinical trials (for review see Herbst et al. (2002) Semin. Oncol. 29:66-77).

The most studied target for tumor anti-angiogenic treatment is the dominant process regulating angiogenesis in human i.e., the interaction of vascular endothelial growth factor (VEGF) with its receptor (VEGFR). Agents which regulate VEGFR pro-angiogenic action include (i) antibodies directed at the VEGF protein itself or to the receptor (e.g., rhuMAb VEGF); (ii) small molecule compounds directed to the VEGFR tyrosine kinase (e.g., ZD6474 and SU5416); (iii) VEGFR targeted ribozymes.

Other novel angiogenesis inhibitors include 2-Methoxyestradiol (2-ME2) a natural metabolite of estradiol that possesses unique anti-tumor and anti-angiogenic properties and angiostatin and endostatin-proteolytic cleavage fragments of plasminogen and collagen XVIII, respectively.

Though promising in pre-clinical models, to date systemic administration of all anti-angiogenic agents tested in clinical trials, have shown limited rate of success and considerable toxicities including thrombocytopenia, leukopenia and hemoptysis. These results suggest that there may be limits to the use of current tumor anti-angiogenic agents as therapy for advanced malignancies. O'Reilly et al. have shown that the latency between the initiation of anti-angiogenic therapy and antitumor effect may result in initial tumor progression before response to therapy [O'Reilly S et al. (1998) Proc Am Soc Clin Oncol 17:217a]. Furthermore, recent studies suggest that the regulation of angiogenesis may differ among capillary beds, suggesting that anti-angiogenic therapy may need to be optimized on an organ/tissue-specific basis [Arap et al. (1998) Science 279:377-380].

Interestingly, poor results have also been obtained when anti-angiogenic therapy (e.g., heparin, heparin-peptide treatment) directed at smooth muscle cell to proliferation has been practiced on myocardial ischemia in patients with coronary artery disease [Liu et al., Circulation, 79: 1374-1387 (1989); Goldman et al., Atherosclerosis, 65: 215-225 (1987); Wolinsky et al., JACC, 15 (2): 475-481 (1990)]. Various limitations associated with the use of such agents for the treatment of cardiovascular diseases included: (i) systemic toxicity creating intolerable level of risk for patients with cardiovascular diseases; (ii) interference with vascular wound healing following surgery; (iii) possible damage to surrounding endothelium and/or other medial smooth muscle cells.

In-light of these and the inherent obstacles associated with systemic administration of anti-angiogenic factors (i.e., manufacturing limitations based on in-vitro instability and high doses required; and peak kinetics of bolus administration attributing to sub-optimal effects) limit the effective use of angiogenic factors in treating neo-vascularization associated diseases.

With the identification of new genes that regulate the angiogenic process, somatic gene therapy has been attempted to overcome these limitations. Although, great efforts have been directed towards developing methods for gene therapy of cancer, cardiovascular and peripheral vascular diseases, there is still major obstacles to effective and specific gene delivery [for review see, Feldman A L. (2000) Cancer 89(6): 1181-94] In general, the main limiting factor of gene therapy with a gene of interest, using a recombinant viral vector as a shuttle is the ability to specifically direct the gene of interest to the target tissue.

Attempts to overcome these limitations included the use of tissue-specific promoters conjugated to cytotoxic genes. For example, endothelial cell targeting of a cytotoxic gene, expressed under the control endothelial-specific promoters has been described by Jagger et al who used the KDR or E-selectin promoter to express TNFα specifically in endothelial cells [Jaggar R T. Et al. Hum Gene Ther (1997) 8(18): 2239-47]. Ozaki et al used the von-Willebrand factor (vWF) promoter to deliver herpes simplex virus thymidine kinase (HSV-tk) to HUVEC [Hum Gene Ther (1996) 7(13):1483-90]. However, these promoters showed only weak activity and did not allow for high levels of expression.

An alternate approach presented by Kong and Crystal included a tumor specific expression of anti-angiogenic factors. To date, however, the toxicity of recombinant forms of endogenous anti-angiogenic agents has not been demonstrated although some synthetic anti-angiogenic agents have been associated with toxicity in preclinical models [Kong and Crystal (1998) J. Natl. Cancer Inst. 90:273-76].

Angiostatin has also been used as a possible anti-angiogenic agent (Falkman et al, Cell 1997 Jan. 24; 88(2):277-85), however due to the redundancy of factors involved in regulation of angiogenesis in tumors, it is highly unlikely that angiostatin therapy alone would be effective.

There is thus a widely recognized need for, and it would be highly advantageous to have a novel approach for efficiently down-regulating angiogenesis in specific tissue regions of a subject while being devoid of the toxic side effects characterizing prior art anti-angiogenesis approaches.

SUMMARY OF THE INVENTION

According to one aspect of the present invention there is provided a nucleic acid construct comprising: (a) a first polynucleotide region encoding a chimeric polypeptide including a ligand binding domain fused to an effector domain of an apoptosis signaling molecule; and (b) a second polynucleotide region encoding a cis acting regulatory element being for directing expression of the chimeric polypeptide in a specific tissue or cell; wherein the ligand binding domain is selected such that it is capable of binding a ligand present in the specific tissue or cell, whereas binding of the ligand to the ligand binding domain activates the effector domain of the apoptosis signaling molecule.

According to further features in preferred embodiments of the invention described below, there is provided a mammalian cell transformed with the nucleic acid construct described above.

According to another aspect of the present invention there is provided a method of down-regulating angiogenesis in a tissue of a subject, the method comprising administering to the subject a nucleic acid construct designed and configured for generating apoptosis in a sub-population of angiogenic cells, the nucleic acid construct including: (a) a first polynucleotide region encoding a chimeric polypeptide including a ligand binding domain fused to an effector domain of an apoptosis signaling molecule; and (b) a second polynucleotide region encoding a cis acting regulatory element being for directing expression of the chimeric polypeptide in the sub-population of angiogenic cells; wherein the ligand binding domain is selected such that it is capable of binding a ligand present in, or provided to, the sub-population of angiogenic cells, whereas binding of the ligand to the ligand binding domain activates the effector domain of the apoptosis signaling molecule, thereby down-regulating angiogenesis in the tissue.

According to further features in preferred embodiments of the invention described below, the method further comprising administering the ligand to the subject in a manner suitable for providing the ligand to the sub-population of angiogenic cells.

According to yet another aspect of the present invention there is provided method of down-regulating angiogenesis in a tissue of a subject, the method comprising: (a) administering to the subject a nucleic acid construct designed and configured for generating apoptosis in a sub-population of angiogenic cells, the nucleic acid construct including: (i) a first polynucleotide region encoding a chimeric polypeptide including a ligand binding domain fused to an effector domain of an apoptosis signaling molecule, wherein the effector domain is selected such that it is activated following binding of a ligand to the ligand binding domain; and (ii) a second polynucleotide region encoding a cis acting regulatory element being for directing expression of the chimeric polypeptide in the sub-population of angiogenic cells; and (b) administering to the subject the ligand, thereby down-regulating angiogenesis in the tissue.

According to still further features in the described preferred embodiments the administering the ligand to the subject is effected by a method selected from the group consisting of: (i) systemic in-vivo administration; (ii) ex-vivo administration to cells removed from a body of the subject, the cells subsequently reintroduced into the body of the subject; and (iii) local in-vivo administration.

According to still further features in the described preferred embodiments the cis-acting regulatory element is an endothelial cell-specific or periendothelial cell-specific promoter selected from the group consisting of the PPE-1 promoter, the PPE-1-3x promoter, the TIE-1 promoter, the TIE-2 promoter, the Endoglin promoter, the von Willerband promoter, the KDR/flk-1 promoter, The FLT-1 promoter, the Egr-1 promoter, the ICAM-1 promoter, the VCAM-1 promoter, the PECAM-1 promoter, the CArG box element and aortic carboxypeptidase-like protein (ACLP) promoter.

According to still further features in the described preferred embodiments the ligand binding domain is a ligand-binding domain of a cell-surface receptor.

According to still further features in the described preferred embodiments the cell-surface receptor is selected from the group consisting of a receptor tyrosine kinase, a receptor serine kinase, a receptor threonine kinase, a cell adhesion molecule and a phosphatase receptor.

According to still further features in the described preferred embodiments the apoptosis signaling molecule is selected from the group consisting of Fas and TNFR.

According to still another aspect of the present invention there is provided a pharmaceutical composition for down regulating angiogenesis in a tissue of a subject, the pharmaceutical composition comprising as an active ingredient a nucleic acid construct designed and configured for generating apoptosis in a subpopulation of angiogenic cells and a pharmaceutical acceptable carrier, the nucleic acid construct including: (a) a first polynucleotide region encoding a chimeric polypeptide including a ligand binding domain fused to an effector domain of an apoptosis signaling molecule; and (b) a second polynucleotide region encoding a cis acting regulatory element being for directing expression of the chimeric polypeptide in the subpopulation of angiogenic cells; wherein the ligand binding domain is selected such that it is capable of binding a ligand present in the specific tissue or cell, whereas binding of the ligand to the ligand binding domain activates the effector domain of the apoptosis signaling molecule.

According to an additional aspect of the present invention there is provided a method of treating a disease or condition associated with excessive neo-vascularization, the method comprising administering a therapeutically effective amount of a nucleic acid construct designed and configured for generating apoptosis in a sub-population of angiogenic cells, the nucleic acid construct including: (i) a first polynucleotide region encoding a chimeric polypeptide including a ligand to binding domain fused to an effector domain of an apoptosis signaling molecule; and (ii) a second polynucleotide region encoding a cis acting regulatory element being for directing expression of the chimeric polypeptide in the sub-population of angiogenic cells; wherein the ligand binding domain is selected such that it is capable of binding a ligand present in, or provided to, the sub-population of angiogenic cells, whereas binding of the ligand to the ligand binding domain activates the effector domain of the apoptosis signaling molecule, thereby down-regulating angiogenesis in the tissue and treating the disease or condition associated with excessive neo-vascularization.

According to yet an additional aspect of the present invention there is provided a method of treating a tumor in a subject, the method comprising administering a therapeutically effective amount of a nucleic acid construct designed and configured for generating apoptosis in cells of the tumor, the nucleic acid construct including: (i) a first polynucleotide region encoding a chimeric polypeptide including a ligand binding domain fused to an effector domain of an apoptosis signaling molecule; and (ii) a second polynucleotide region encoding a cis acting regulatory element being for directing expression of the chimeric polypeptide in the cells of the tumor; wherein the ligand binding domain is selected such that it is capable of binding a ligand present in, or provided to, the cells of the tumor, whereas binding of the ligand to the ligand binding domain activates the effector domain of the apoptosis signaling molecule to thereby direct apoptosis in the cells of the tumor.

According to still further features in the described preferred embodiments the method further comprising administering the ligand to the subject in a manner suitable for providing the ligand to the cells of the tumor.

According to still further features in the described preferred embodiments the cis acting regulatory element is selected from the group consisting of the gastrin-releasing peptide (GRP) promoter, the hTERT promoter, the Hexokinase type II promoter and the L-plastin promoter.

The present invention successfully addresses the shortcomings of the presently known configurations by providing a novel approach for efficiently downregulating angiogenesis and tumor cell proliferation in a specific and targeted manner.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the Drawings:

FIGS. 2a-b illustrate apoptotic activity of the pro-apoptotic genes, Fas chimera and TNFR1. FIG. 2a—illustrates Bovine Aortic Endothelial Cells (BAEC) transfected with either pcDNA-3-TNFR1 (lower panel) or control empty vector (upper panel) and an expression plasmid encoding GFP. FIG. 2b—illustrates 293 Cells transfected with either pcDNA-3-Fas-c (lower panel) or control empty vector (upper panel) and an expression plasmid encoding GFP. Transfected cells were visualized using fluorescence microscopy and apoptotic activity was morphologically determined.

FIGS. 3a-f are electron microscopy images of BAEC cells transfected with pro-apoptotic genes. 24 hours post transfection, BAEC cells were fixed in 2.5% glutaraldehyde and processed. Presented are cells in successive stages of the apoptotic process.

FIG. 8 shows a dose response effect of TNFα administration on Fas-chimera mediated apoptosis. BAEC were infected with Ad-PPE-1-3x-Fas-c. 48 h post infection TNF was added to the growth medium (at the indicated dose). Viability was determined by the crystal violet assay 24 h thereafter.

FIGS. 9*a*-*e* are photomicrographs illustrating an endothelial cell-specific apoptosis mediated by the cooperative action of TNFα ligand and Fas-c receptor. The indicated cells were incubated in the presence or absence of TNFα (10 ng/ml) 48 h following infection with Ad-PPE-1-3x-Fas-c; crystal violet staining was effected 72 h post infection.

FIG. 10*b*—NSF infected with a control virus. FIG. 10*c*—NSF infected with Ad-CMV-Fas-chimera. FIG. 10*d*—NSF infected with Ad-CMV-Fas-chimera and incubated with TNF (10 ng/ml).

FIG. 11*a*—tumor areas, measured during treatment period. FIG. 11*b*—tumor weights at end of treatment period. FIG. 11*c*—an image representing the state of the tumor in the Ad-PPE-1-3x-Fas-c treated mouse and the control mouse.

DESCRIPTION OF THE PREFERRED EMBODIMENTS

Figure 1A:
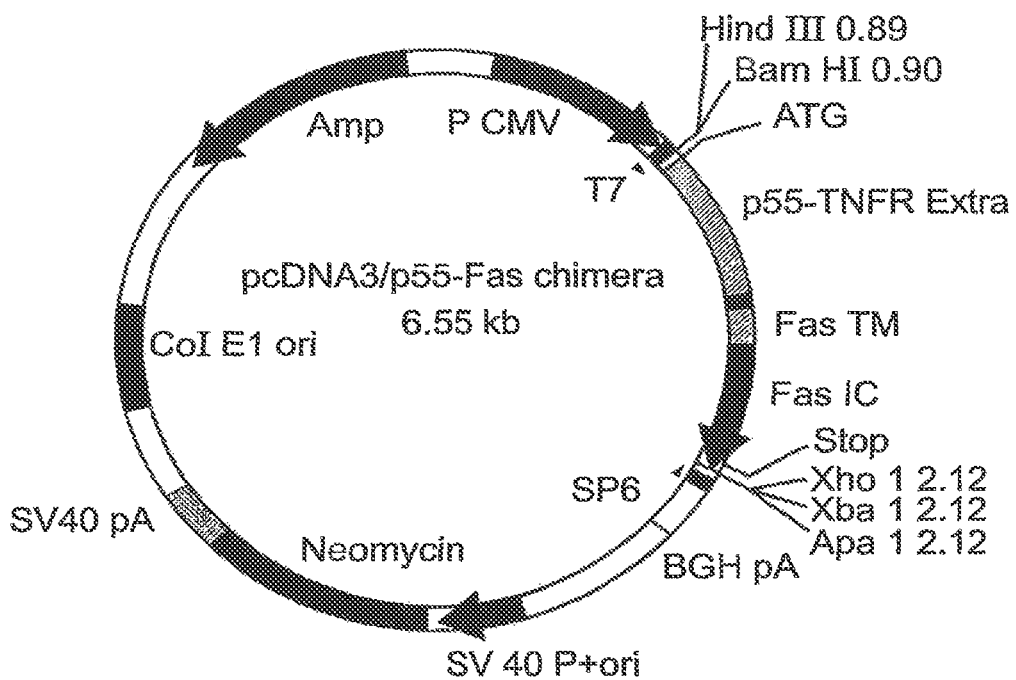
FIGS. 1a-b are schematic illustrations of Fas chimera gene constructed from the extracellular region of TNFR1 and the trans-membrane and intracellular regions of Fas and cloned into pcDNA3 plasmid (a) or into adenoviral vectors (b).

The present invention is of nucleic acid constructs and methods, which can be used to treat diseases characterized by excessive or aberrant neovascularization or cell growth. Specifically, the present invention can be used to specifically target and kill cells involved in angiogenesis, thus enabling down-regulation of angiogenesis and anti-tumor therapy.

The principles and operation of the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

One of the most fundamental goals of anti-angiogenic therapy is to return foci of proliferating microvessels to their normal resting state, and to prevent their re-growth.

To date, anti-angiogenic therapy approaches, which employ systemic administration of anti-angiogenic agents have been employed with limited success mostly due to the toxic side effects which lead to the formation of thrombocytopenia, leukopenia and/or hemoptysis in the treated individual. The toxic side effects associated with prior art approaches is a result of non-specific expression of the anti-angiogenic agents employed and exposure of healthy tissue to these agents or the redundancy and thus non-effectiveness of the anti-angiogenic agents used.

While reducing the present invention to practice, the present inventors have uncovered that a combination of tissue-specific expression and specific activation of a pro-apoptotic agent enables selective apoptosis of cells involved in angiogenesis without exposing non-targeted tissue or cells to these agents, thus, avoiding the toxic side effects and redundancy characterizing prior art treatment approaches.

Thus, according to one aspect of the present invention there is provided a method of down-regulating angiogenesis in a tissue of a subject. As used herein, the phrase "down-regulating angiogenesis" refers to either slowing down or stopping the angiogenic process, which lead to formation of new blood vessels.

The method according to this aspect of the present invention is effected by administering to the subject a nucleic acid construct designed and configured for generating apoptosis in a sub-population of angiogenic cells. As used herein, the phrase "angiogenic cells" refers to any cells, which participate or contribute to the process of angiogenesis. Thus, angiogenic cells include but are not limited to, endothelial cells, smooth muscle cells.

In order to direct specific expression of an apoptotic agent in a subpopulation of angiogenic cells, the nucleic acid construct of the present invention includes a first polynucleotide region encoding a chimeric polypeptide including a ligand binding domain which can be, for example, a cell-surface receptor domain of a receptor tyrosine kinase, a receptor serine kinase, a receptor threonine kinase, a cell adhesion molecule or a phosphatase receptor fused to an effector domain of an apoptosis signaling molecule such as, for example, Fas, TNFR, and TRAIL.

Such a chimeric polypeptide can include any ligand binding domain fused to any apoptosis signaling domain as long as activation of the ligand binding domain, i.e., via ligand binding, triggers apoptosis signaling via the effector domain of the apoptosis signaling molecule.

Selection of the ligand binding domain and the apoptosis signaling domain fused thereto is affected according to the type of angiogenic cell targeted for apoptosis. For example, when targeting specific subset of endothelial cells (e.g., proliferating endothelial cells, or endothelial cells exhibiting a tumorous phenotype), the chimeric polypeptide includes a ligand binding domain capable of binding a ligand naturally present in the environment of such endothelial cells and preferably not present in endothelial cells of other non-targeted tissues (e.g., TNF, VEGF). Such a ligand can be secreted by endothelial cells (autocrine), secreted by neighboring tumor cells (paracrine) or specifically targeted to these endothelial cells.

Examples of suitable chimeric polypeptides are provided in Examples 2 of the Examples section which follows. Preferably, the chimeric polypeptide is the Fas-c chimera which is described in detail in Examples 2-4 of the Examples section which follows.

The use of such a chimeric polypeptide is particularly advantageous, since, as shown in the Examples section hereinunder, it enables efficient and robust activation of apoptosis in a specific subset of angiogenic cells while avoiding activation in other subset of cells, which are not targeted for apoptosis.

To further enhance cell specificity of apoptosis, the nucleic acid construct of the present invention further includes a second polynucleotide region, which encodes a cis acting regulatory element (e.g., promoter and/or enhancer) capable of directing expression of the chimeric polypeptide in the sub-population of angiogenic cells.

Examples of suitable promoters/enhancers which can be utilized by the nucleic acid construct of the present invention include the endothelial-specific promoters: preproendothelin-1, PPE-1 promoter (Harats D, J Clin Invest. 1995 March; 95(3):1335-44)., the PPE-1-3x promoter [PCT/IL01/01059; Varda-Bloom N, Gene Ther 2001 June; 8(11):819-27], the TIE-1 (S79347, S79346) and the TIE-2 (U53603) promoters [Sato T N, Proc Natl Acad Sci USA 1993 Oct. 15; 90(20): 9355-8], the Endoglin promoter [Y11653; Rius C, Blood 1998 Dec. 15; 92(12):4677-90], the von Willerbrand factor [AF152417; Collins C J Proc Natl Acad Sci USA 1987 July; 84(13):4393-7], the KDR/flk-1 promoter [X89777, X89776; Ronicke V, Circ Res 1996 August; 79(2):277-85], The FLT-1 promoter [D64016 AJ224863; Morishita K: J Biol Chem 1995 Nov. 17; 270(46):27948-53], the Egr-1 promoter [AJ245926; Sukhatme V P, Oncogene Res 1987 September-October; 1(4):343-55], the E-selectin promoter [Y12462; Collins T J Biol Chem 1991 Feb. 5; 266(4):2466-73], The endothelial adhesion molecules promoters: ICAM-1 [X84737; Horley K J EMBO J 1989 October; 8(10):2889-96], VCAM-1 [M92431; Iademarco M F, J Biol Chem 1992 Aug. 15; 267(23):16323-9], PECAM-1 [AJ313330×96849; CD31, Newman P J, Science 1990 Mar. 9; 247(4947):1219-22], the vascular smooth-muscle-specific elements: CArG box X53154 and aortic carboxypeptidase-like protein (ACLP) promoter [AF332596; Layne M D, *Circ Res.* 2002; 90: 728-736] and Aortic Preferentially Expressed Gene-1 [Yen-Hsu Chen J. Biol. Chem., Vol. 276, Issue 50, 47658-47663, Dec. 14, 2001].

Preferably, the promoter utilized by the construct of the present invention is functional in proliferating angiogenic cells, or angiogenic cells of a particular phenotype (e.g., tumorous). A promoter highly suitable for use with the present invention is the PPE-1-3x promoter which is further described in the Examples section which follows. A vector construct most suitable for use with the present invention is the widely used adenoviral vector and its derivatives.

It was discovered that a novel configuration of the PPE-1 enhancer sequence of the present invention endows promoter sequences with an unexpected and highly specific activity in endothelial cells participating in angiogenesis. Thus, according to one aspect of the present invention there is provided an isolated polynucleotide functional as an endothelial cell specific promoter in a mammal such as a human being. The isolated polynucleotide includes an enhancer element including one or more copies of the sequence set forth in SEQ ID NO:6 and preferably one or more copies of the sequence set forth in SEQ ID NO: 8, which as is illustrated in the Examples section which follows, plays an important role in regulating expression in endothelial cells participating in angiogenesis.

One specific and novel sequence configuration of an enhancer element utilizable by the present invention is illustrated in SEQ ID NO:7.

For purposes of this specification and the accompanying claims, the term "enhancer" refers to any polynucleotide sequence which increases the transcriptional efficiency of a promoter.

According to some embodiments of the invention, the isolated polynucleotide includes contiguous copies of SEQ ID NOs:6 and/or 8. Such sequences are preferably positioned in a head-to-tail orientation, although, the enhancer element of the present invention can also include one or more copies of a specific portion of the sequence of SEQ ID NO:6 or 8, in an inverted orientation, e.g., by using sequences complementary to SEQ ID NO:6 or 8 in construction of the enhancer element.

Thus, it is postulated that a minimal configuration of an enhancer element according to the present invention is an isolated polynucleotide as set forth in SEQ ID NO: 8. This enhancer is anticipated to function with a wide variety of promoters, including but not limited to endothelial specific promoters (e.g. PPE-1; SEQ ID NO.: 1) and constitutive promoters, for example viral promoters such as those derived from CMV and SV-40. This enhancer should be capable of imparting endothelial specificity to a wide variety of promoters. The enhancer element may be augmented, for example by addition of one or more copies of the sequence set forth in SEQ ID NO:6. These additional sequences may be added contiguously or non-contiguously to the sequence of SEQ ID NO.: 8.

The present invention further includes a method of expressing a nucleic acid sequence of interest in endothelial cells employing a construct which relies upon an enhancer element including at least one copy of the sequence set forth in SEQ ID NO: 8 and a promoter to direct high level expression of the sequence of interest specifically to endothelial cells.

The promoter sequences generated according to the teachings of the present invention are particularly useful in regulating angiogenesis in a tissue. As illustrated in the Examples section which follows, the modified 3X (SEQ. ID. NO:7) containing promoter sequence of the present invention and the unmodified PPE-1 promoter are both expressed in metastatic foci of the LLC model. Thus, use of a construct including the 3X element in a gene therapy context can be expected to maximize delivery to tumors while minimizing toxic effects on surrounding normal tissue.

The nucleic acid construct of the present invention can further include additional polynucleotide sequences such as for example, sequences encoding selection markers or reporter polypeptides, sequences encoding origin of replication in bacteria, sequences that allow for translation of several proteins from a single mRNA (IRES), sequences for genomic integration of the promoter-chimeric polypeptide encoding region and/or sequences generally included in mammalian expression vector such as pcDNA3, pcDNA3.1(+/−), pZeoSV2(+/−), pSecTag2, pDisplay, pEF/myc/cyto, pCMV/myc/cyto, pCR3.1, which are available from Invitrogen, pCI which is available from Promega, pBK-RSV and pBK-CMV which are available from Stratagene, pTRES which is available from Clontech, and their derivatives.

Preferably, the nucleic acid construct of the present invention is administered to the subject via, for example, systemic administration routes or via oral, rectal, transmucosal (especially transnasal), intestinal or parenteral administration routes. Systemic administration includes intramuscular, subcutaneous and intramedullary injections as well as intrathecal, direct intraventricular, intravenous, inrtaperitoneal, intranasal, intraocular injections or intra-tumoral.

Preferably, the subject is a mammal, more preferably, a human being, most preferably, a human being suffering from diseases characterized by excessive or abnormal neovascularization such as that characterizing tumor growth, proliferating diabetic retinopathy, arthritis and the like.

The nucleic acid constructs of the present invention can be administered to the subject per se or as part (active ingredient) of a pharmaceutical composition.

The prior art teaches of a number of delivery strategies which can be used to efficiently deliver naked or carrier provided polynucleotides into a wide variety of cell types (see, for example, Luft (1998) J Mol Med 76(2): 75-6; Kronenwett et al. (1998) Blood 91(3): 852-62; Rajur et al. (1997) Bioconjug Chem 8(6): 935-40; Lavigne et al. (1997) Biochem Biophys Res Commun 237(3): 566-71 and Aoki et al. (1997) Biochem Biophys Res Commun 231(3): 540-5).

As used herein a "pharmaceutical composition" refers to a preparation of one or more of the active ingredients or agents described herein with other chemical components such as physiologically suitable carriers and excipients. The purpose of a pharmaceutical composition is to facilitate administration of a compound to an organism.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered nucleic acid construct. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include oral, rectal, transmucosal, especially transnasal, intestinal or parenteral delivery, including intramuscular, subcutaneous and intramedullary injections as well as intrathecal, direct intraventricular, intravenous, inrtaperitoneal, intranasal, or intraocular injections.

Alternately, one may administer the pharmaceutical composition in a local rather than systemic manner, for example, via injection of the pharmaceutical composition directly into a tissue region of a patient. In the context of the present invention, administration directly into tumor tissue is a relevant example of local administration.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries, which facilitate processing of the active ingredients into preparations which can be used pharmaceutically. Proper formulation is dependent upon the route of administration chosen.

For injection, the active ingredient of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The pharmaceutical composition described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The pharmaceutical composition of the present invention may also be formulated in rectal compositions such as suppositories or retention enemas, using, e.g., conventional suppository bases such as cocoa butter or other glycerides.

Pharmaceutical compositions suitable for use in context of the present invention include compositions wherein the active ingredients are contained in an amount effective to achieve the intended purpose. More specifically, a therapeutically effective amount means an amount of active ingredients (e.g. antisense oligonucleotide) effective to prevent, alleviate or ameliorate symptoms of a disorder (e.g., progressive loss of bone mass) or prolong the survival of the subject being treated.

Determination of a therapeutically effective amount is well within the capability of those skilled in the art, especially in light of the detailed disclosure provided herein.

For any preparation used in the methods of the invention, the therapeutically effective amount or dose can be estimated initially from in vitro and cell culture assays. For example, a dose can be formulated in an animal model, such as the murine Src deficient model of osteopetrosis (Boyce et al. (1992) J. Clin. Invest. 90, 1622-1627; Lowe et al. (1993) Proc. Natl. Acad. Sci. USA 90, 4485-4489; Soriano et al. (1991) Cell 64, 693-702), to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Dosage amount and interval may be adjusted individually to levels of the active ingredient are sufficient to retard tumor progression (minimal effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or diminution of the disease state is achieved.

The amount of a composition to be administered will, of course, be dependent on the subject being treated, the severity of the affliction, the manner of administration, the judgment of the prescribing physician, etc.

Compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as if further detailed above.

The pharmaceutical compositions of the present invention may further include any additional ingredients which may improve the uptake of the nucleic acid construct by the cells, expression of the chimeric polypeptide encoded by the nucleic acid construct in the cells, or the activity of the expressed chimeric polypeptide.

For example, the uptake of adenoviral vectors into EC cells can be enhanced by treating the vectors with engineered antibodies or small peptides. Such "adenobody" treatment, was shown effective in directing adenovirus constructs to EGF receptors on cells (Watkins et al 1997, Gene Therapy 4:1004-1012). In addition, Nicklin et al have shown that A small peptide, isolated via phage display, increased specificity and efficiency of vectors in endothelial cells and decreased the expression in liver cells in culture (Nicklin et al 2000, Circulation 102:231-237). In a recent study, an FGF retargeted adenoviral vector reduced the toxicity of tk in mice (Printz et al 2000, Human Gene Therapy 11:191-204).

It will be appreciated that although targeting of cells exposed to the ligand is preferred, the present invention also envisages expression of the nucleic acid construct of the present invention in cells which are not exposed to, or naturally affected by the ligand. In such cases, the method of the present invention includes the step of administering such a ligand to the cells transformed. Such administration can be effected by using any of the above described administration methods. Preferably, the ligand is administrated in a cell targeted manner, using for example antibody conjugated targeting, such that activation of apoptosis signaling is highly specific. This approach of apoptosis activation is described in more detail in the Examples section which follows.

Thus, the present invention provides nucleic acid constructs, pharmaceutical compositions including such constructs and methods of utilizing such constructs for downregulating angiogenesis in tissue regions characterized by excessive or abnormal angiogenesis.

Since the present invention enables targeted expression in specific cell subsets, it can also be modified and used in for treating various tumors.

Thus, according to another aspect of the present invention there is provided a method of treating tumors.

The method according to this aspect of the present invention is effected by expressing in tumor cells the chimeric polypeptide described above.

Thus according to this aspect of the present invention, expression of the polypeptide chimera is directed by a tumor specific element, such as, but not limited to, the gastrin-releasing peptide (GRP) promoter [AF293321S3; Morimoto E Anticancer Res 2001 January-February; 21(1A):329-31], the hTERT promoter [AH007699; Gu J, Gene Ther 2002 January; 9(1):30-7], the Hexokinase type II promoter [AF148512; Katabi M M, Hum Gene Ther. 1999 Jan. 20; 10(2):155-64.], or the L-plastin promoter [L05490, AH002870, MMU82611; Peng X Y, Cancer Res. 2001 Jun. 1; 61(11):4405-13].

Expression of the polypeptide chimera (e.g., Fas-c) in tumor cells activates apoptosis in these cells and thus leads to cell death, which in turn causes tumor growth slowdown or arrest, and possibly tumor shrinkage.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures in recombinant DNA technology described below are those well known and commonly employed in the art. Standard techniques are used for cloning, DNA and RNA isolation, amplification and purification. Generally enzymatic reactions involving DNA ligase, DNA polymerase, restriction endonucleases and the like are performed according to the manufacturers' specifications. These techniques and various other techniques are generally performed according to Sambrook et al., Molecular Cloning—A Laboratory Manual, Cold Spring Harbor Laboratory, Cold Spring Harbor, N.Y. (1989). The manual is hereinafter referred to as "Sambrook". Other general references are provided throughout this document. The procedures therein are believed to be well known in the art and are provided for the convenience of the reader. All the information contained therein is incorporated herein by reference.

Example 1

In-Vitro Assay for Pro-Apoptotic Gene Activity in Endothelial Cells (BAEC) and 293 Cells In cancer treatment, anti-angiogenic therapy targets the evolving vasculature which nourishes the growing tumor [Folkman J. N Engl J Med (1995) 333(26):1757-63]. As the research of apoptosis, or programmed cell death, has progressed, numerous genes that encode selective and efficient cell death regulators have been identified [Strasser et al. Annu Rev Biochem (2000) 69:217-45.].

The present study screened several pro-apoptotic genes in order to identify an agent most suitable for anti-angiogenic therapy. Several pro-apoptotic genes including MORT1 (FADD—Fas associated death domain protein, GenBank Accession number NM_003824), RIP (receptor-interacting-protein, GenBank Accession number U25995), CASH (c-FLIP, GenBank Accession number AF010127), MACH (caspase 8 GenBank Accession number X98172), CPP32 (caspase 3, GenBank Accession number U13737), caspase 9 (U60521) and Fas-chimera (Fas-c), a previously described fusion of two "death receptors", constructed from the extra-cellular region of TNFR1 and the trans-membrane and intracellular regions of Fas [Boldin M P et al. J Biol Chem (1995) 270(14):7795-8, see FIG. 1a) were PCR amplified and cloned into the pcDNA3 (Invitrogen, Inc.) mammalian expression vector using well known prior art cloning techniques.

Figure 4:
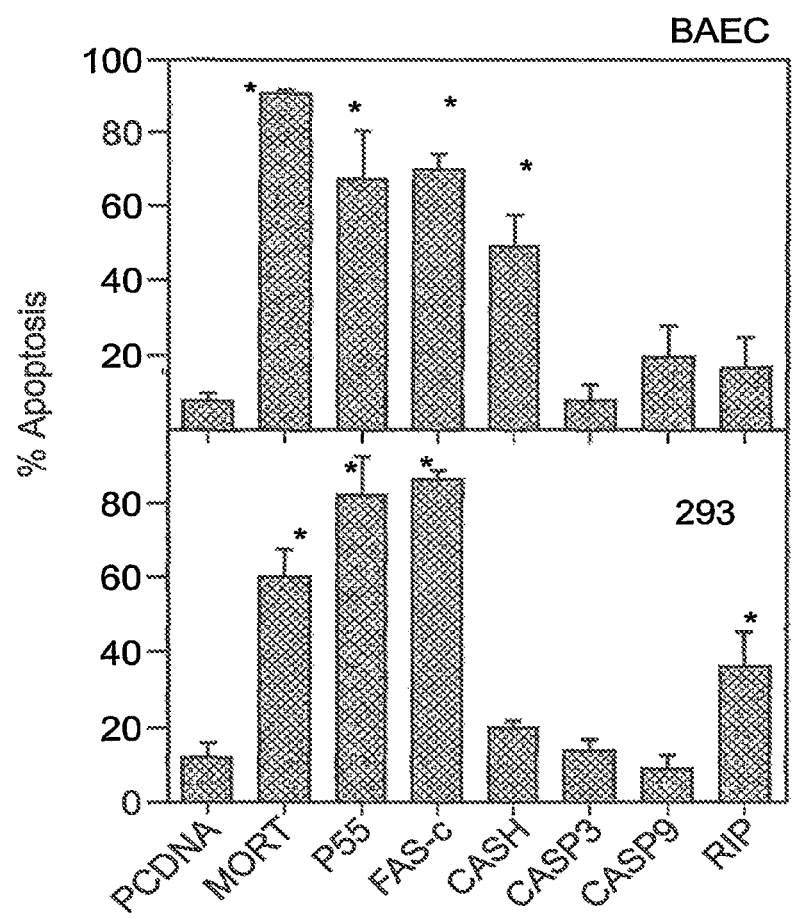
FIG. 4 are histograms quantifying apoptotic activity of the indicated pro-apoptotic genes in transfected BAEC and 293 cells.

These pro-apoptotic gene constructs were co-expressed along with pGFP in BAEC (Bovine Aortic Endothelial Cells) and 293 cells, which were used as non-endothelial control cells. 24 hours post transfection, cells were analyzed using fluorescent microscopy. Apoptotic cells were identified based on typical morphology, (i.e., small and round shape) using fluorescence microscopy (FIGS. 2a-b). Further assessment of the apoptotic phenotype was effected using electron microscopy (FIGS. 3a-f). Quantification of the apoptotic effect showed that MORT1, TNFR1 and Fas-chimera induced the highest apoptotic activity in BAEC and 293 cells (FIG. 4a-b). Caspase 3 and 9 were less potent in this respect, probably because they were in an inactive zymogen form. Based on these results, the Fas-chimera (Fas-c) gene was selected for the generation of an adenoviral-vector to be used in anti-angiogenic therapy.

Example 2

Figure 1B:
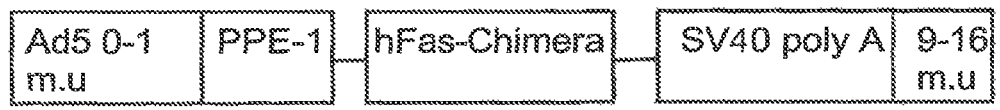
Figure 1B:
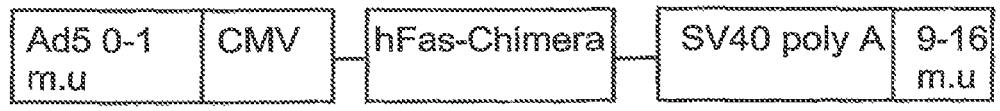
Figure 5A:
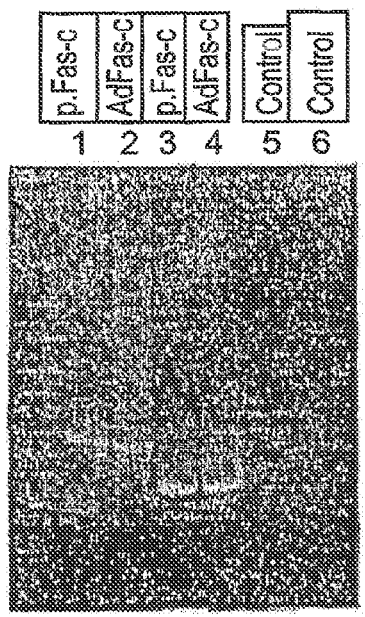
FIG. 5a represents a PCR analysis of AdPPE-Fas-c. Lanes 1-2—PCR products obtained using primers encompassing the PPE-1 promoter and Fas-c gene. Lanes 3-4—PCR products obtained using Fas-c primers. Lanes 5-6—PCR products obtained in the absence of template DNA.

Production of Recombinant Adenoviruses Encoding Fas-Chimera Under the Control of the Modified PPE-1 Promoter A cDNA encoding a full length Fas-chimera was subcloned into the plasmid pPACPPE1-3x containing the modified pre-proendothelin1 promoter (see FIG. 1b). Recombinant adenoviruses were produced by co-transfection of this plasmid with pJM17 plasmid into human embryonic kidney 293 cells. Successful viral cloning was verified via PCR amplification (FIG. 5a).

Figure 5B:
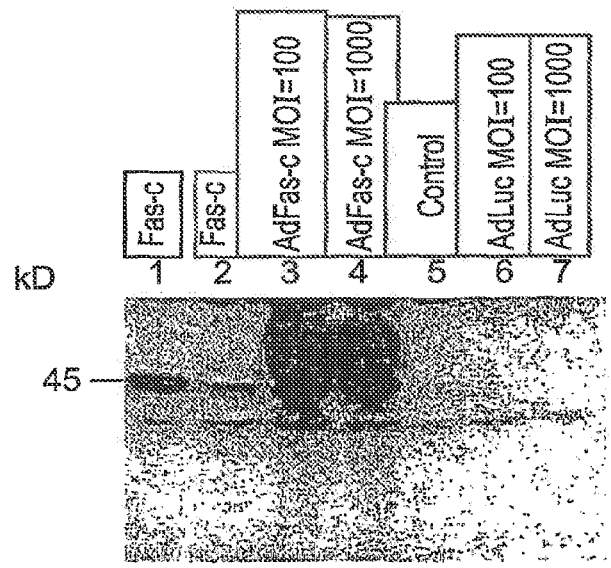
FIG. 5b is a western blot analysis of AdPPE-Fas-c transfected BAEC cells. Protein samples were resolved by SDS-PAGE, transferred to nitrocellulose membrane and probed with a polyclonal antibody directed against the extracellular portion of TNFR1. Lane 1-2—pcDNA3-Fas-c BAEC transfected cells (positive control). Lane 3-4—BAEC cells transfected with the indicated MOI of AdPPE-Fas-c viruses. Lane 5—non-transfected cells. Lane 6-7—BAEC cells transfected with the indicated MOI of AdPPE-Luc.

In order to determine the expression of Fas-c in the target cells, endothelial BAEC cells were transduced with the indicated titer of Ad-PPE-Fas-c. 72 h post transduction cells were lysed and cellular proteins resolved using a non-reducing SDS-PAGE gel. Western blot analysis was performed using anti-TNFR1 antibody (Sc-7895, Santa-Cruz Biotech). As demonstrated in FIG. 5b, a prominent band migrating at 45 kD was clearly evident and its expression was dose-dependent, suggesting correct folding and expression of the chimeric protein. In contrast, no corresponding bands were evident in non-transduced endothelial cells or in cells transduced with control empty viral vector. Thus, these results confirmed that the adenoviral-mediated gene transfer of Fas-c results in transgene expression in the target cells.

Example 3

Ad-PPE-Fas-c Expression Induces Apoptosis in Endothelial Cells

Figure 6A:
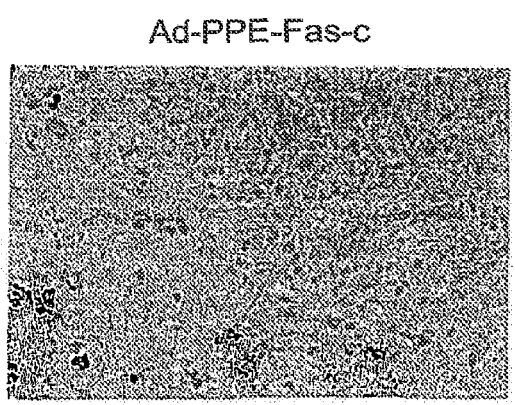
FIGS. 6*a*-*d* are photomicrographs illustrating the effect of Fas-chimera over-expression on apoptosis of endothelial cells. BAEC cells were infected with: Ad-PPE-1-3x-Fas-chimera (FIG. 6*a*); Ad-PPE-1-3x-luciferase (FIG. 6*b*); Ad-PPE-1-3x-Fas-chimera and Ad-PPE1-3x-GFP (FIG. 6*c*); Ad-PPE-1-3x-luciferase and Ad-PPE-1-3x-GFP; each at MOI 1000 (FIG. 6*d*). Photomicrographs were taken 72 h post infection at ×10 magnification.
Figure 6B:
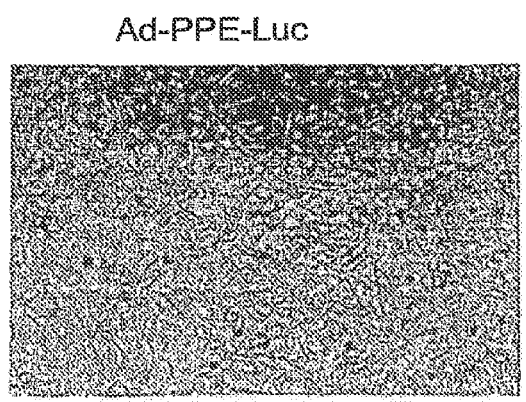

The ability of Ad-PPE-Fas chimera to induce apoptosis of endothelial cells was determined. As shown in FIGS. 6a-b, pre-proendothelin directed, adenovirus-mediated transduction of endothelial cells resulted in an evident and massive cell death; HUVEC and BAEC infected with Ad-PPE-Fas-c ($10^3$ MOI) had morphological features of adherent cells undergoing apoptosis including membrane blebbing, rounding and shrinking and detachment from the culture dish. In contrast, cells infected with control viruses at the same MOI, maintained normal appearance and growth rate. Cells transduced with 100 MOI presented only a minimal degree of cell death (data not shown).

Figure 6C:
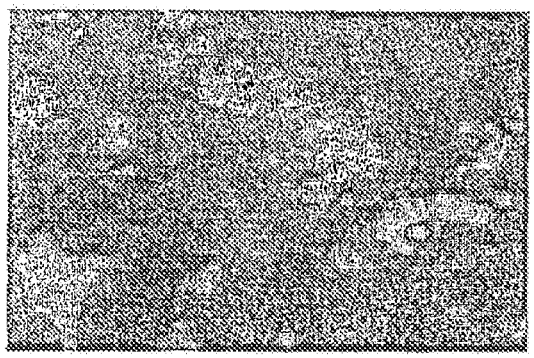
Figure 6D:
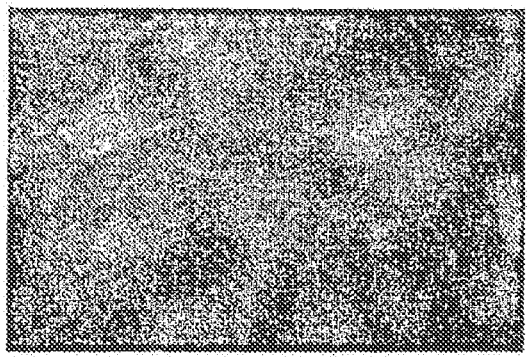

Further assessment of the cytotoxic properties of Ad-PPE-Fas-c was effected by expressing this virus in cells expressing the reporter gene GFP under the control of the PPE-1 promoter. As is evident from FIGS. 6*c-d*, most of the transduced cells acquired a typical apoptotic appearance 72 hours following transduction, whereas cells co-transduced with control virus and Ad-PPE-GFP appeared normal.

Figure 7:
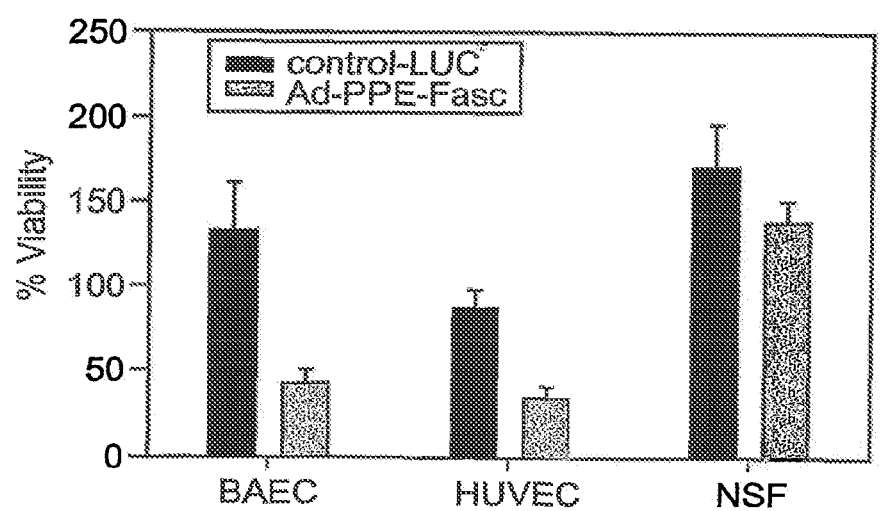
FIG. 7 is a histogram illustrating apoptotic specific effect of Ad-PPE-1-3x-Fas-chimera on endothelial cells. Viability of endothelial (BAEC, HUVEC) and non-endothelial (Normal skin fibroblasts-NSF) cells was quantified by crystal violet staining 72 h post infection with either Ad-PPE-1-3x-Fas-chimera or control (luciferase) virus.
Figure 9C:
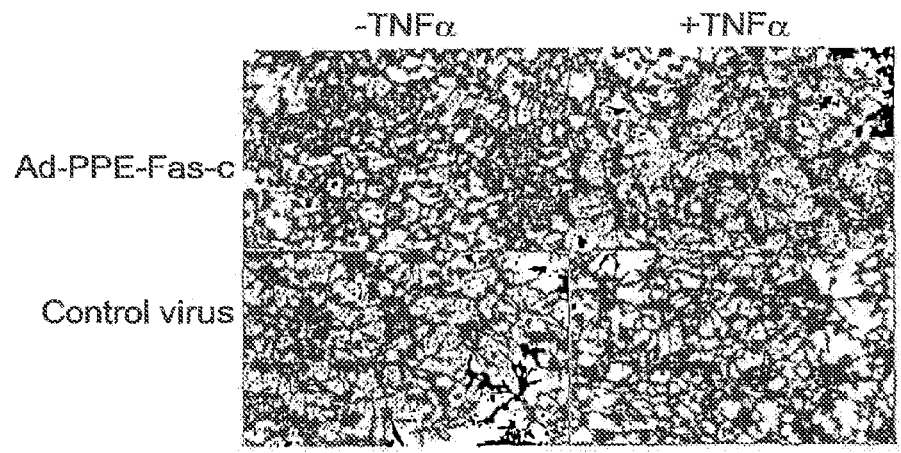
Figure 9D:
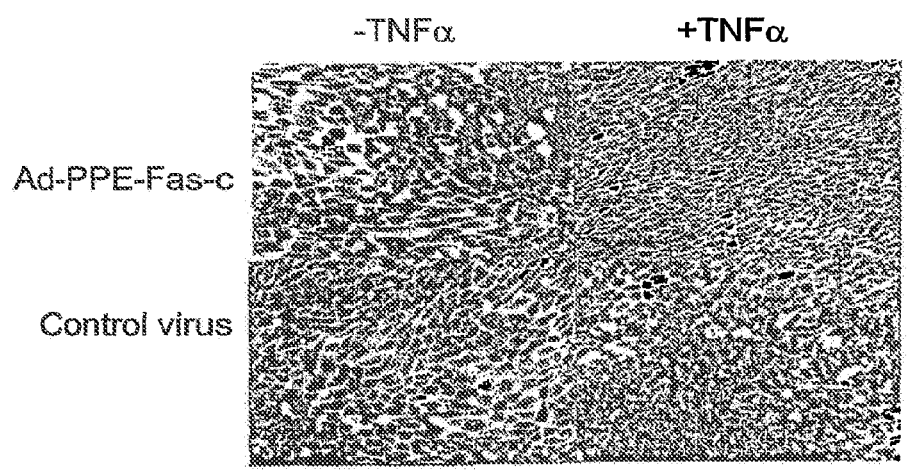
Figure 9E:
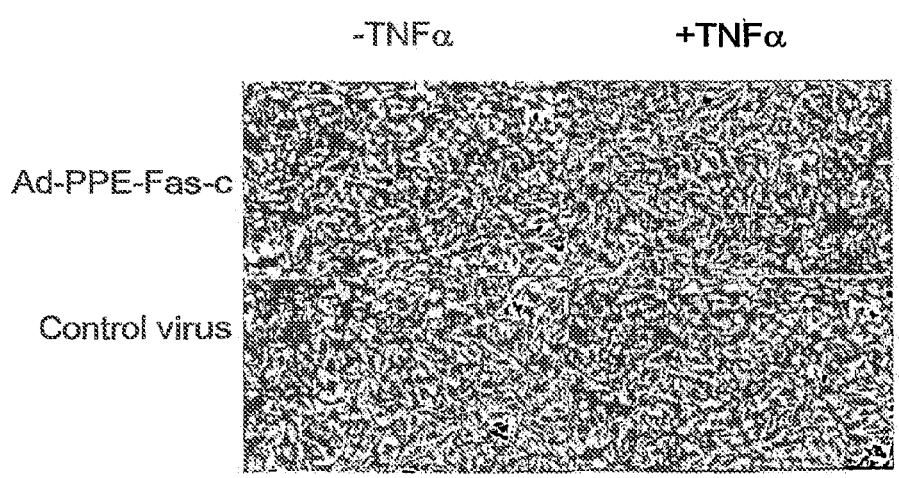

The cytotoxic effect of Fas-c was quantified using crystal violet staining. As shown in FIG. 7, infection of BAEC and HUVEC with Ad-PPE-Fas-c resulted in mortality rates of 57% and 65%, respectively, while the control virus did not affect cell viability.

The endothelial cell specificity of the pro-apoptotic vector Ad-PPE-Fas- was demonstrated by infecting NSF (normal skin fibroblasts) with this vector. These cells, which express low levels of PPE-1 [Varda-Bloom, N. et al. Gene Ther 8, 819-27. (2001)] were not affected by infection with Ad-PPE-Fas-c. In contrast, the recombinant vector Ad-CMV-Fas-c induced apoptotic in these cells.

Example 4

Co-Administraton of Ad-PPE-Fas-c Receptor and TNFα Ligand Augments the Pro-Apoptotic Effect in a Selective Manner The ability of TNFα to augment the apoptotic effect in Fas-c expressing cells was investigated. Human TNFα was added to an endothelial cell culture 48 h-post virus infection with Ad-PPE-Fas-c (MOI of 100). Cell viability was assayed 24 h later. As shown in FIG. 8, TNFα (10 ng/ml) induced a 73% decrease in viabilty of Ad-PPE-Fas-c infected cells, whereas no significant mortality was effected by TNFα alone or in cells infected with control virus (Ad-Luc).

Figure 10A:
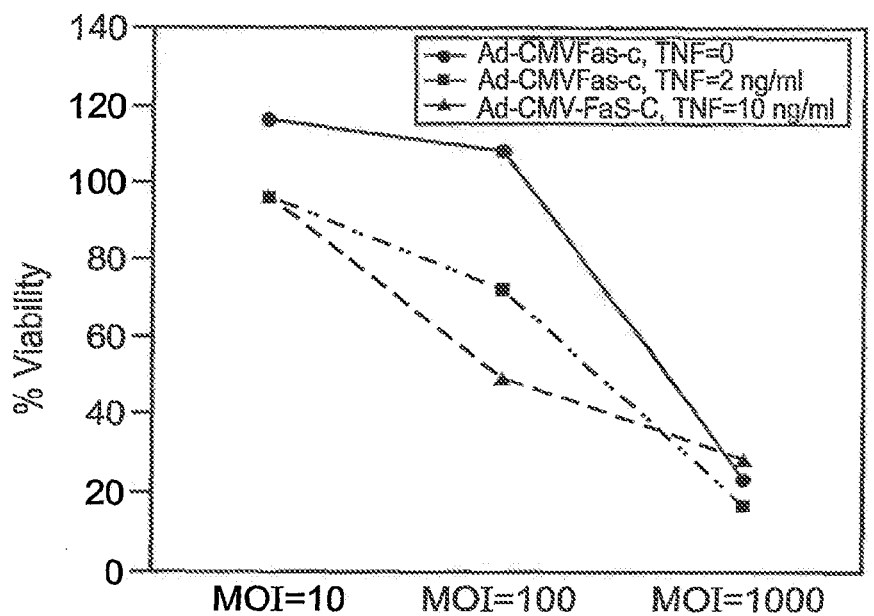
FIG. 10*a* is a dose response curve illustrating the TNFα-dependent apoptotic effect of Ad-CMV-Fas-c on endothelial cells. Viability of BAEC cells infected with the indicated MOI of Ad-CMV-Fas-chimera was determined following incubation with TNFα.

To substantiate the effect of TNFα, cell specificity was addressed. NSF (normal skin fibroblasts), DA3 (mouse mammary adenocarcinoma), D122 (Lewis lung carcinoma) and B16 melanoma cells were infected with Ad-PPE-Fas-c or a control virus. 48 hours later, culture was supplemented with TNFα and cell morphology was assessed following staining with crystal violet. As shown in FIGS. 9*a-e*, non-endothelial cells infected with Ad-PPE-Fas-c displayed normal appearance and were not affected by TNF. On the other hand, adenoviral mediated infection of BAEC with Fas-c resulted in marked decrease in cell viability when TNF was added. The non-selective apoptotic activity of Fas-c driven by CMV promoter is demonstrated in FIG. 10*a* which illustrates the TNF-dependent apoptotic effect of Ad-CMV-Fas-c on endothelial cells. Viability of BAEC cells infected with the indicated MOI of Ad-CMV-Fas-chimera was determined following incubation with TNF.

Figures 10B, 10C, 10D:
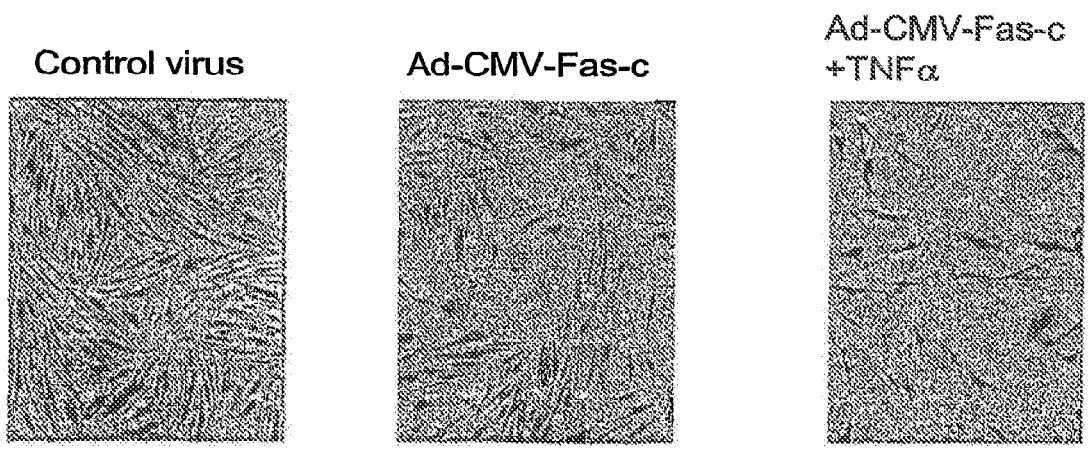
FIGS. 10*b*-*d* illustrate the apoptotic effect of TNFα ligand and Ad-CMV-Fas-chimera on the non-endothelial cells NSF.

Notably, the non-endothelial-specific vector Ad-CMV-Fas-c caused TNFα-dependent apoptosis of both endothelial and non-endothelial cells (FIGS. 10*b-d*).

Example 5

Ad-PPE1-Fas-c Induces In-Vivo Growth Retardation of B16 Melanoma in Mice

The B16 melanoma mouse model was used in order to test the anti-tumoral effect of Fas-c expressed from the PPE1-3x promoter. B16 melanoma cells ($8\times10^5$) were injected subcutaneously to the flank region of 40 C57b1/6 mice. When the tumor was palpable ($\approx 5\times5$ mm), the mice were randomized into 4 groups as follows: (i) control—saline injection; (ii) control virus (Adeno virus containing luciferase controlled by PPE promoter); (iii) Ad-PPE1-3x-Fas-c-virus containing the Fas-TNF receptor chimeric gene controlled by the pre-proendothelin (PPE) promoter; and (iv) Ad-CMV-Fas-c-virus containing the Fas-TNF receptor chimeric gene controlled by the non-endothelial specific, CMV promoter.

Figure 11A:
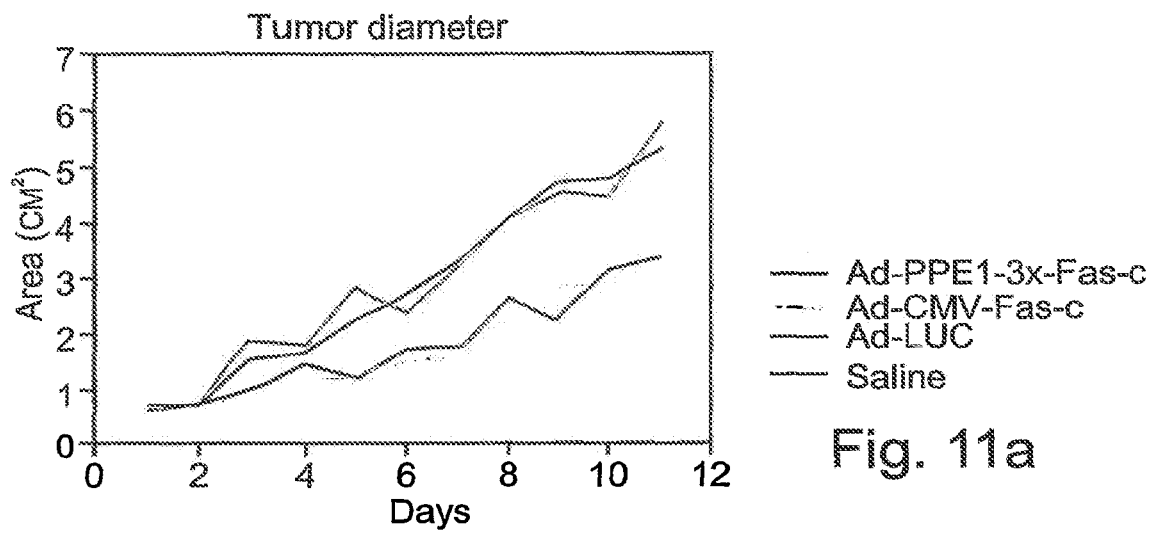
FIGS. 11*a*-*c* illustrate the In-vivo anti-tumoral effect of Ad-PPE-1-3x-Fas-c. Mice inoculated with B16 melanoma cells were injected intravenously with Ad-PPE-1-3x-Fas-c, Ad-CMV-Fas-chimera, control virus or saline when tumor was palpable.
Figure 11B:
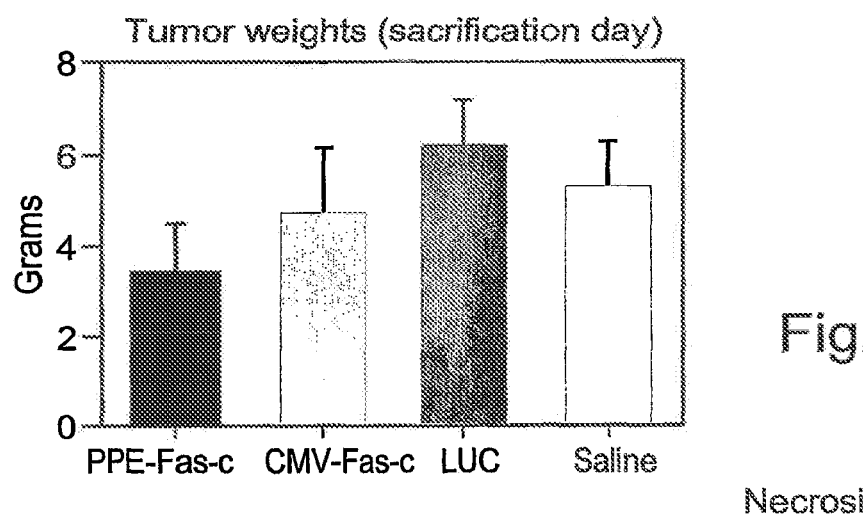
Figure 11C:
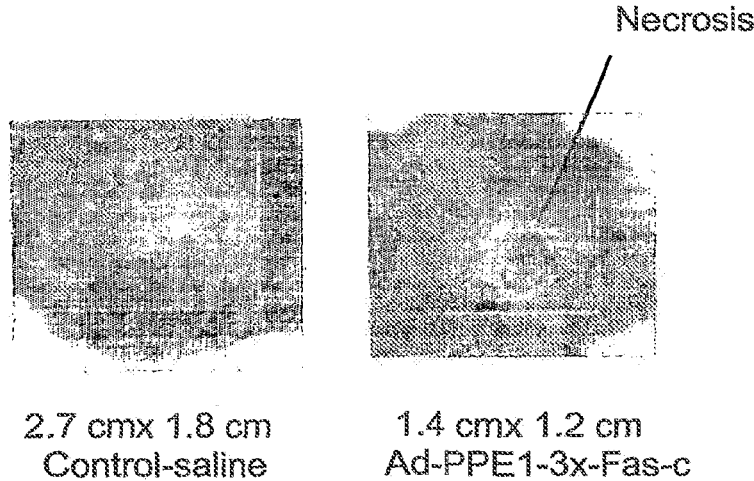

Tumor size (length and width) was measured using a hand caliper. As shown in FIG. 11*a*, tumor size was lower for mice treated with Ad-PPE1-3x-Fas-c or Ad-CMV-Fas-c as compared to control mice. Tumor weights at the end of the treatment period was also lower in the Ad-PPE1-3x-Fas-c treated mice (FIG. 11*b*). Mice injected with Ad-PPE1-3x-Fas-c showed marked necrosis of their tumor (FIG. 11*c*).

Example 6

Modifications of the PPE Promoter

The modified murine PPE-1 promoter was developed by inserting three copies of the positive transcription element discovered by Bu et al (J. Biol Chem. (1997) 272(19): 32613-32622) into the NheI restriction enzyme site located downstream (−286 bp) to the 43 base pairs endogenous positive element (−364 to −320 bp).

The enhancer fragment termed herein "3X" is a triplicate copy of an endogenous sequence element (nucleotide coordinates 407-452 of SEQ ID NO:1) present in the murine PPE-1 promoter. It has been previously shown that induction of PPE-1 promoter activity in vascular endothelial cells depends on the presence of this element Bu et al (J. Biol Chem. (1997) 272(19): 32613-32622). The 3X fragment was synthesized by using two complementary single stranded DNA strands 96 base pares in length (BioTechnology industries; Nes Tziona, Israel), (SEQ ID NO: 2 and 3). The two single stranded DNA fragment were annealed and filled using Klenow fragment (NEB); the resulting double stranded DNA was 145 base pairs long and included Nhe-1 restriction sites (SEQ ID NO: 4).

The 3X fragment was ligated into the murine PPE-1 promoter down stream of endogenous Nhe-1 site using T4 Ligase. The resulting construct was propagated in DH5α compatent cells and a large-scale plasmid preparation was produced using the maxi-prep Qiagene kit.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents, patent applications and sequences identified by their accession numbers mentioned in this specification are herein incorporated in their entirety by reference into the specification, to the same extent as if each individual publication, patent, patent application or sequence identified by their accession number was specifically and individually indicated to be incorporated herein by reference. In addition, citation or identification of any reference in this application shall not be construed as an admission that such reference is available as prior art to the present invention.

What is claimed is:

1. A vector comprising a nucleic acid construct, which comprises:
   a) a first polynucleotide region encoding a chimeric polypeptide comprising a ligand binding domain of TNF Receptor 1 (TNFR1) fused to an effector domain of Fas; and
   b) a second polynucleotide region comprising a PPE-1-3X promoter, which directs expression of the chimeric polypeptide in endothelial cells of angiogenic blood vessels;
   wherein the second polynucleotide region is operably linked to the first polynucleotide region, and wherein the chimeric polypeptide, when expressed, induces apoptosis of the endothelial cells.

2. The vector of claim 1, wherein the ligand binding domain of TNFR1 comprises an extracellular domain of TNFR1.

3. The vector of claim 1, wherein the effector domain of Fas comprises a trans-membrane region and an intracellular region of Fas.

4. The vector of claim 1, wherein the ligand binding domain of TNFR1 is an extracellular domain of TNFR1 and the effector domain of Fas is a trans-membrane region and an intracellular region of Fas.

5. The vector of claim 4, wherein the vector is an adenoviral vector.

6. The vector of claim 5, wherein the adenoviral vector is adenovirus serotype-5.

7. The vector of claim 5, wherein the vector is Ad-PPE-1-3X-Fas-chimera.

8. A pharmaceutical composition comprising the vector of claim 1 and a pharmaceutically acceptable carrier.

9. A method of producing a vector comprising:
   (1) transducing a host cell with a vector comprising a nucleic acid construct which comprises:
      a) a first polynucleotide region encoding a chimeric polypeptide comprising a ligand binding domain of TNF Receptor 1 (TNFR1) fused to an effector domain of Fas; and
      b) a second polynucleotide region comprising a PPE-1-3X promoter, which directs expression of the chimeric polypeptide in endothelial cells of angiogenic blood vessels; wherein the second polynucleotide region is operably linked to the first polynucleotide region, and wherein the chimeric polypeptide, when expressed, induces apoptosis of the endothelial cells;
   (2) expressing the vector in the host cell.

10. The method of claim 9, wherein the ligand binding domain of TNFR1 comprises an extracellular domain of TNFR1.

11. The method of claim 9, wherein the effector domain of Fas comprises a trans-membrane region and an intracellular region of Fas.

12. The method of claim 9, wherein the ligand binding domain of TNFR1 is an extracellular domain of TNFR1 and the effector domain of Fas is a trans-membrane region and an intracellular region of Fas.

13. The method of claim 9, wherein the vector is an adenoviral vector.

14. The method of claim 13, wherein the adenoviral vector is adenovirus serotype-5.

15. The method of claim 13, wherein the vector is Ad-PPE-1-3X-Fas-chimera.

16. The vector of claim 1, wherein the ligand binding domain of TNFR1 consists essentially of an extracellular domain of TNFR1.

17. The vector of claim 1, wherein the effector domain of Fas consists essentially of a trans-membrane region and an intracellular region of Fas.

18. The vector of claim 1, wherein the ligand binding domain of TNFR1 consists of an extracellular domain of TNFR1.

19. The vector of claim 1, wherein the effector domain of Fas consists of a trans-membrane region and an intracellular region of Fas.

20. The vector of claim 1, wherein the chimeric polypeptide consists essentially of an extracellular domain of TNFR1 and a trans-membrane region and an intracellular region of Fas.

\* \* \* \* \*

SEQUENCE LISTING

<160> NUMBER OF SEQ ID NOS: 8

<210> SEQ ID NO 1
<211> LENGTH: 1334
<212> TYPE: DNA
<213> ORGANISM: Mus musculus

<400> SEQUENCE: 1

| | | | | | |
|---|---|---|---|---|---|
| gtgtgtgtgt | gtgtgtgtgt | gtgtgtgtgt | gtgtgtgtgt | gtgtagtgta | cttctgatcg | 60 |
| gcgatactag | ggagataagg | atgtacctga | caaaaccaca | ttgttgttgt | tatcattatt | 120 |
| atttagtttt | ccttccttgc | taactcctga | cggaatcttt | ctcacctcaa | atgcgaagta | 180 |
| ctttagttta | gaaaagactt | ggtggaaggg | gtggtggtgg | aaaagtaggg | tgatcttcca | 240 |
| aactaatctg | gttccccgcc | cgccccagta | gctgggattc | aagagcgaag | agtggggatc | 300 |
| gtccccttgt | ttgatcagaa | agacataaaa | ggaaaatcaa | gtgaacaatg | atcagcccca | 360 |
| cctccacccc | accccctgc  | gcgcgcacaa | tacaatctat | ttaattgtac | ttcatacttt | 420 |
| tcattccaat | ggggtgactt | tgcttctgga | gaaactcttg | attcttgaac | tctggggctg | 480 |
| gcagctagca | aaaggggaag | cgggctgctg | ctctctgcag | gttctgcagc | ggtctctgtc | 540 |
| tagtgggtgt | tttcttttc  | ttagccctgc | ccctggattg | tcagacggcg | ggcgtctgcc | 600 |
| tctgaagtta | gccgtgattt | cctctagagc | cgggtcttat | ctctggctgc | acgttgcctg | 660 |
| tgggtgacta | atcacacaat | aacattgttt | agggctggaa | taaagtcaga | gctgtttacc | 720 |
| cccactctat | aggggttcaa | tataaaaagg | cggcggagaa | ctgtccgagt | cagacgcgtt | 780 |
| cctgcaccgg | cgctgagagc | ctgacccggt | ctgctccgct | gtccttgcgc | gctgcctccc | 840 |
| ggctgcccgc | gacgctttcg | ccccagtgga | agggccactt | gctgaggacc | gcgctgagat | 900 |
| ctaaaaaaa  | aacaaaaaac | aaaaacaaa  | aaacccaga  | ggcgatcaga | gcgaccagac | 960 |
| accgtcctct | tcgttttgca | ttgagttcca | tttgcaaccg | agtttcttt  | ttttcctttt | 1020 |
| tccccactct | tctgacccct | ttgcagaatg | gattattttc | ccgtgatctt | ctctctgctg | 1080 |
| ttcgtgactt | tccaaggagc | tccagaaaca | ggtaggcgcc | acttgcgaat | cttcctactt | 1140 |
| cagcgcagca | gttatcgctt | ctgttttcca | cttttctttc | tttctttct  | ttcattcttt | 1200 |
| ccttttatt  | tatttttta  | attactgaag | ctccagcagc | aagtgcctta | caattaatta | 1260 |
| acttctgtgt | gaagcgaaag | aaataaaacc | cctgtttgaa | tacagctgac | tacaaccgag | 1320 |
| tatcgcatag | cttc       | | | | | 1334 |

<210> SEQ ID NO 2

<400> SEQUENCE: 2

000

<210> SEQ ID NO 3

<400> SEQUENCE: 3

000

<210> SEQ ID NO 4

<400> SEQUENCE: 4

000

<210> SEQ ID NO 5

```
<400> SEQUENCE: 5

000

<210> SEQ ID NO 6
<211> LENGTH: 44
<212> TYPE: DNA
<213> ORGANISM: Artificial sequence
<220> FEATURE:
<223> OTHER INFORMATION: Murine endothelial specific enhancer element

<400> SEQUENCE: 6
gtacttcata cttttcattc caatggggtg actttgcttc tgga                44

<210> SEQ ID NO 7
<211> LENGTH: 143
<212> TYPE: DNA
<213> ORGANISM: Artificial sequence
<220> FEATURE:
<223> OTHER INFORMATION: A triplicate copy of a murine enhancer sequence
      originated from the PPE-1 promoter

<400> SEQUENCE: 7
gtacttcata cttttcattc caatggggtg actttgcttc tggagggtga ctttgcttct      60
ggagccagta cttcatactt ttcattgtac ttcatacttt tcattccaat ggggtgactt     120
tgcttctgga ggctagctgc cag                                             143

<210> SEQ ID NO 8
<211> LENGTH: 47
<212> TYPE: DNA
<213> ORGANISM: Artificial sequence
<220> FEATURE:
<223> OTHER INFORMATION: EDC fragment

<400> SEQUENCE: 8
ctggagggtg actttgcttc tggagccagt acttcatact tttcatt              47
```